United States Patent [19]

Ostberg

[11] Patent Number: 5,565,354
[45] Date of Patent: Oct. 15, 1996

[54] PRODUCTION OF HUMAN MONOCLONAL ANTIBODIES SPECIFIC FOR HEPATITIS B SURFACE ANTIGEN

[75] Inventor: Lars G. Ostberg, Convent Station, N.J.

[73] Assignee: Sandoz Ltd., Basel, Switzerland

[21] Appl. No.: 259,372

[22] Filed: Jun. 14, 1994

Related U.S. Application Data

[63] Continuation of Ser. No. 871,426, Apr. 21, 1992, abandoned, which is a continuation-in-part of Ser. No. 676,036, Mar. 27, 1991, abandoned, which is a continuation-in-part of Ser. No. 538,796, Jun. 15, 1990, abandoned, which is a continuation of Ser. No. 192,754, May 11, 1988, abandoned, which is a continuation-in-part of Ser. No. 925,196, Oct. 31, 1986, abandoned, which is a continuation-in-part of Ser. No. 904,517, Sep. 5, 1986, abandoned.

[51] Int. Cl.$^6$ ............................. C12N 5/20; C07K 16/08
[52] U.S. Cl. ............................. 435/240.27; 530/388.15; 530/388.3; 435/70.21; 424/149.1
[58] Field of Search ..................... 530/388.15, 388.3; 435/70.21, 240.27; 935/99, 100; 424/149.1

[56] References Cited

U.S. PATENT DOCUMENTS

| | | |
|---|---|---|
| 4,346,073 | 8/1982 | Aronson et al. . |
| 4,491,632 | 1/1985 | Wands et al. . |
| 4,608,337 | 8/1986 | Croce et al. . |
| 4,634,666 | 1/1987 | Engleman et al. . |
| 4,883,752 | 11/1989 | Eda et al. . |

FOREIGN PATENT DOCUMENTS

| | | |
|---|---|---|
| 0389983 | 10/1990 | European Pat. Off. . |
| 2113715 | 8/1983 | United Kingdom . |
| 9114703 | 10/1991 | WIPO . |

OTHER PUBLICATIONS

Ogata et al (1993) Proc. Nat'l. Acad. Sci. 90: 3014–3018.
Matsui et al. (1982) Nichi Dai Ishi (J. Nihon Univ. Med. Assoc.) 41(12): 1163–1171 (English translation, pp. 1–23).
Matsui et al (1982) Biol. Abstr. 77(6): 4766, Abstract# 43590.
Goldstein et al. (1986) Transplantation 42: 507–511.
Ehrlich et al. (1992) Hum. Antibod. Hybridomas 3: 2–7.
Perillo et al (1990) N. Engl. J. Med. 323: 295–301.
Janssen et al (1994) Antiviral Res. 23: 251–257.
Hoofnagle et al "Serologic Responses in HB; In Viral Hepatitis" (Vyas et al. eds.) Franklin Press., 1978, pp. 219–242.
Roitt (1991) "Essential Immunology", Blackwell Scientific Publications, Oxford, pp. 65–68 & 74.
Burragi et al (1985) Cancer Res. 45: 3378–3387.
Goding J. W. (1983) "Monoclonal Antibodies", Academic Press, Inc., Orlando, pp. 118–125.
Davidsohn et al (1974) "Clinical Diagnosis By Laboratory Methods", W. B. Saunders Co., Philadelphia, pp. 848–851 & 861–865.
Roitt (1991) "Essential Immunology", Blackwell Scientific Publications, Oxford, pp. 68–75.
Cotran et al (1989) "Robbins Pathologic Basis of Disease", W. B. Saunders Company, Philadelphia, pp. 927–928.
Todo et al (1991) Hepatology 13: 619–626.
Demetris et al (1986) Am. J. Pathol. 125: 161–172.
Starzi et al (1989) Transplantation Proceedings 21: 2197–2200.
Andris et al (1992) J. Immunology 149: 4053–4059.
Kozbor et al (1984) J. Immunol. 133: 3001–3005.
Teng et al (1983) Proc Nat'l Acad Sci.80: 7308–7312.
Steinitz et al (1979) J. Clin. Lab. Immunol. 2: 1–7.
Matsui et al (1982) Nichidai Igaku Zasshi 41(12); 1163–1172 [& Biol. Abstr. 77(6); 4766, #43590].
Wands et al (1981) Gastroenterology 80: 225–232.
Imai et al (1982) J. Immunol. 128: 69–72.
Ichimori, et al., Biochem. & Biophysical Res. Comm., vol. 129, pp. 26–33 1985.
Stricker, E. A. M. et al. 1985. "A Human Monoclonal IgG1λ Anti–Hepatitis B Surface Antibody" *Scan. J. Immunol.* 22:337–343.
Harada, K. et al. 1989 "Human–Human Hybridomas Secreting Hepatitis B Virus Neutralizing Antibodies" *Bio/Technology* 7:374–377.
Ichimori, Y. et al. 1987. "Establishment of Hybridoma Secreting Human Monoclonal Antibody Against Hepatitis B Virus Surface Antigen" *Bioch. bioph. Res. Comm.* 142(3):805–812.

*Primary Examiner*—Paula K. Hutzell
*Assistant Examiner*—Ray F. Ebert
*Attorney, Agent, or Firm*—Townsend and Townsend and Crew LLP

[57] ABSTRACT

Monoclonal antibodies effective for the diagnosis and treatment of diseases caused by infection with hepatitis B have been prepared from a cell line obtained by fusing a xenogeneic hybridoma designated SPAZ 4 with blood cells of a patient immunized with hepatitis B vaccine. The invention also provides cocktails of the above monoclonal antibodies specific for different epitopes of hepatitis B surface antigen.

9 Claims, 2 Drawing Sheets

PRODUCTION OF HUMAN MONOCLONAL ANTIBODIES SPECIFIC FOR HEPATITIS B SURFACE ANTIGEN

This is a Continuation of application Ser. No. 07/871,426, filed Apr. 21, 1992, now abandoned, which is a continuation-in-part of Ser. No. 07/676,036, filed Mar. 27, 1991 (now abandoned), which is a continuation-in-part of Ser. No. 07/538,796, filed Jun. 15, 1990 (now abandoned), which is a continuation of Ser. No. 07/192,754, filed May 11, 1988 (now abandoned), which is a continuation-in-part of Ser. No. 06/925,196, filed Oct. 31, 1986 (now abandoned), which is a continuation-in-part of Ser. No. 06/904,517, filed Sep. 5, 1986 (now abandoned).

The present invention concerns hybridoma cell lines which produce human antibodies which neutralize the hepatitis B virus, methods for producing the cell lines, antibodies produced by the cell lines, and uses of the antibodies, particularly therapeutically.

The making of hybridoma cell lines for the purpose of producing monoclonal antibodies is in general well known at this time to researchers in this art. The present invention concerns the obtaining of human monoclonal antibodies effective in particular against hepatitis B surface antigen (HBsAg), such antibodies being prepared according to a generally applicable method described by the applicant in *Hybridoma* 2(4):361 (1983) and United Kingdom Patent Application 2,113,715A, published Aug. 10, 1983. More particularly, it has been found that a hybridoma cell line comprising a parent rodent immortalizing cell, such as a murine myeloma cell, e.g. SP-2, fused to a human partner cell results in an immortalizing xenogeneic hybridoma cell. This xenogeneic hybridoma cell may be fused to a cell capable of producing an anti-HBsAg human antibody, resulting in a novel trioma cell line capable of generating human antibody effective against such antigen in the human. Alternately, when greater stability is desired, a trioma cell line which preferably no longer has the capability of producing its own antibody is made and this trioma is then fused with a further cell capable of producing useful against said antigen so as to obtain a still more stable hybridoma (quadroma) which produces antibody against the antigen.

The applicant's publications earlier referred to describe the preparation of a xenogeneic hybridoma referred to as SPAZ 4, prepared from drug resistant cell line SP-2 obtainable, e.g., from the NIGMS Human Genetic Mutant Cell Repository Ref. GM35669A (see U.S. DHHS 1982 Catalog of Cell Lines). Preparation of SPAZ 4 is summarized as follows. The SP-2 cell line is fused with normal human peripheral lymphocytes by conventional techniques. A large number of hybrids is obtained and, after approximately five weeks, five clones are selected which show fast growth and no antibody production. These cells are selected for resistance to 8-azaguianine and with three of these lines it is possible to obtain mutants which are resistant to 20 μg/ml of 8-azaguanine. These cells are at the same time sensitive to Hypoxanthine-Aminopterin-Thymidine (HAT) medium which showed that they had lost their ability to produce hypoxanthine phosphoribosyl transferase. One of these cell lines is SPAZ 4.

Cell line SPAZ 4 may be fused with cells obtained from the blood of persons immunized with hepatitis B vaccine to obtain hybridoma cell lines which provide positive cultures when standard selection procedures are used involving binding of antibodies to relevant viral antigens. It is preferred that said positive cultures be placed through a second selection process in which different subtypes of the virus are used for antigen preparation. This provides an opportunity to pinpoint the exact antigenic determinant recognized by the antibody.

The cell lines resulting from the fusion of a xenogeneic hybridoma and the human monoclonal antibody producing cell (trioma) are therefore useful in providing monoclonal antibodies capable of effective activity in neutralizing a virus causing hepatitis, and said antibodies can therefore prevent the spread of hepatitis through e.g. blood transfusion. They can also be used to give initial protection to newborn babies or exposed individuals earlier than a vaccine could be effective. Anti-hepatitis antibodies may be used to protect immunosuppressed patients, including transplantation patients, from recurrent hepatitis. This is most significant in cases of hepatitis B positive liver recipients. Further, the antibodies can be used in diagnostic assays.

It has also been found that antibody fragments, such as Fab fragments can also bind to hepatitis B virus surface antigen. These fragments also make up part of this invention.

Specific antibodies which have been made according to this invention include PE1-1, ZM1-1, ZM1-2, MD3-4 and LO3-3, each of these antibodies being of the $IgG_1$ class.

The cell line producing PE1-1 was deposited at the American Type Culture Collection 12301 Parklawn Drive, Rockville, Md. 20852 on Oct. 16, 1986 and given accession number ATCC HB 9234; the cell line producing ZM1-1 was deposited as ATCC HB 9191 on Sep. 4, 1986 and the cell line producing ZM1-2 was deposited as ATCC HB 9192 on Sep. 4, 1986. The address of the American Type Culture Collection is 12301 Parklawn Drive, Rockville, Md. 20852.

The cell lines of the present invention all behave as typical (mouse×human)×human hybridomas and produce their respective antibodies in concentrations ranging up to 25 mg/l in standard suspension culture.

Figure 1:
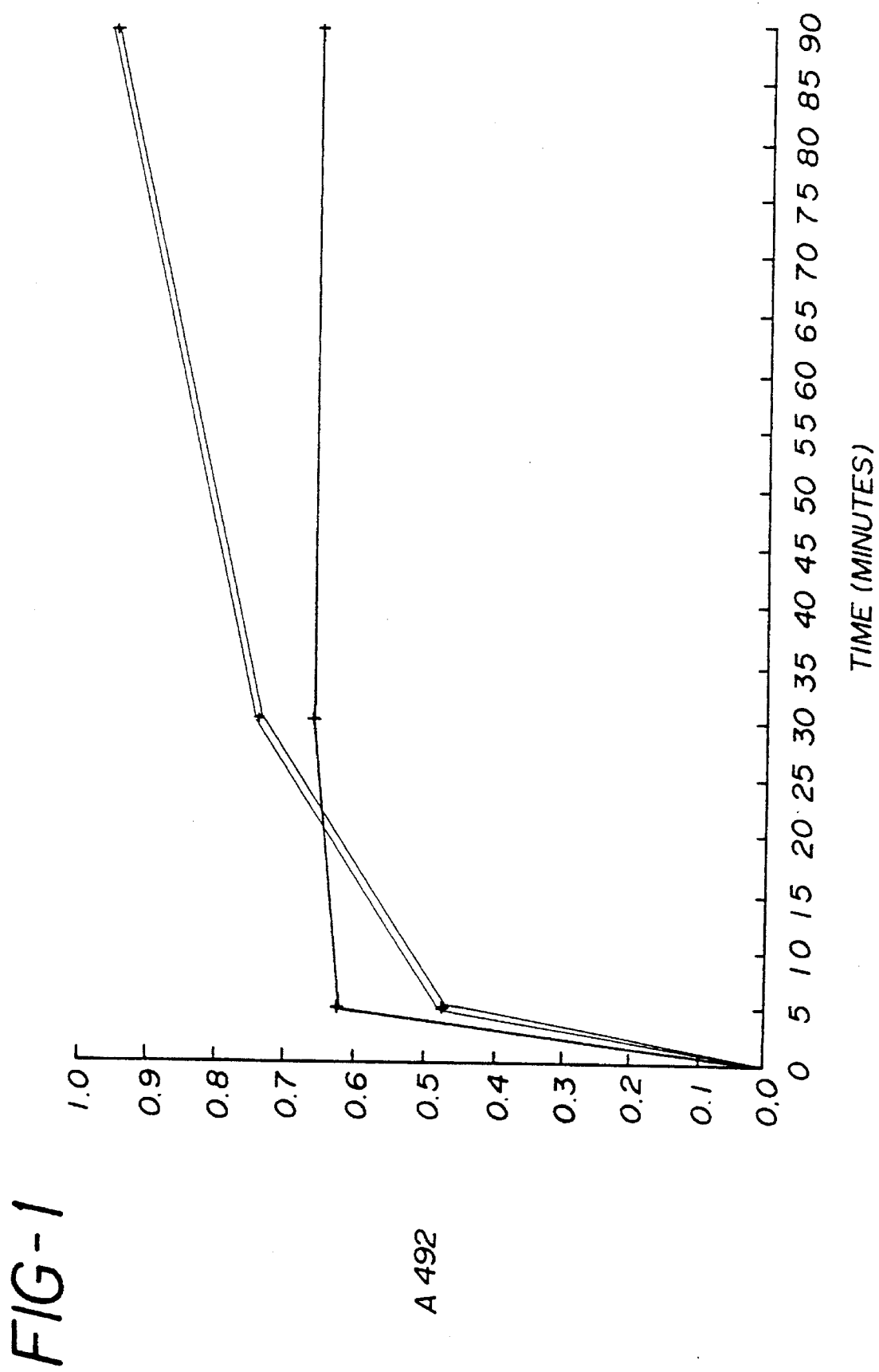
FIG. 1 shows the results of a direct binding enzyme linked immunoassay comparing binding kinetics of antibody PE1-1 (shown by the single line) and antibody ZM1-2 (double line). Details are given in Example 4A.

Throughout the specification and claims, the same designation is given to both the cell line and the antibody it produces, i.e. cell line PE1-1 produces monoclonal antibody PE1-1; cell line ZM1-1 produces monoclonal antibody ZM1-1, etc. It is felt that one of ordinary skill in the art will understand whether the cell line or the antibody is being discussed.

Monoclonal antibody and cell line PE1-1 has also been referred to by the inventor and the inventor's assignee as OST 577 and 64-577. Likewise, monoclonal antibody and cell line ZM1-2 have also been referred to as 265-695, and monoclonal antibody and cell line LO3-3 have been referred to as 266-215.

The antibodies and antibody fragments obtained according to this invention have good specificity for hepatitis B surface antigen in in vitro ELISA binding assays.

As the antibodies of the present invention are of human origin, they are advantageously used in human therapy, as no allergenic response develops with repeated therapy, as occurs with murine or ovine antibodies. Thus, another aspect of this invention is a method of treating hepatitis B through the administration of one or more of the aforementioned antibodies. It has been found that repeated doses of approximately 10–40 mg antibody will substantially reduce the amount of circulating HBsAg. Additional doses were found to decrease the amount of HBsAg levels to below the detectable limits of antigen tests.

Another aspect of this invention is a cocktail of two or more monoclonal antibodies. This mixture is particularly suited for administration to patients who carry a non-wild type strain of hepatitis B virus which does not bind well with a given single monoclonal antibody. For example, one compassionate need patient who suffered from hepatocellular carcinoma and chronic hepatitis B was given antibody PE1-1 prior to liver transplantation, and repeated doses thereafter. (Details are given below in Example 5). After approximately four and one-half months of treatment, low levels of serum HBsAg could be detected with a polyclonal antibody, but not with PE1-1. Polymerase chain reaction (PCR) DNA analysis of the 230 base pair region of the HBsAg gene corresponding to the putative monoclonal antibody binding domain was performed. The PCR DNA was cloned into M13 bacteriophage and the resulting DNA was sequenced. Analysis of clones from each of the serum samples revealed two variant sequences when compared to PCR DNA from the original liver and pre-antibody therapy. The variant DNA codes for two different amino acids in the S protein of HBsAg and also codes for a stop codon (UAG) in the viral polymerase gene. Both variant genes contain an amino acid change resulting in the substitution of arginine for glycine in a conserved peptide domain.

Since the monoclonal antibodies PE1-1, ZM1-2, ZM1-1, MD3-4 and L03-3 have been shown to bind to different epitopes, and at least one of the monoclonal antibodies has been found to bind to every variant virus tested to date to a sufficient extent to render it clinically useful, another aspect of this invention is a cocktail of two or more of the monoclonal antibodies selected from the group consisting of: PE1-1, ZM1-2, ZM1-1, MD3-4 and L03-3. Particularly preferred are cocktails of two monoclonal antibodies, especially the mixture of PE1-1 and ZM1-2 and the mixture of PE1-1 and L03-3. The ratio of the monoclonal antibodies present in the mixture may vary depending on many factors apparent to one of ordinary skill in the art and include: the genotype of the hepatitis virus or viruses present in the patient's serum, the relative binding strengths of the antibodies chosen, the epitopes to which the chosen antibodies bind, and economic considerations. Generally, the antibodies will be present in a ratio ranging from 1:99, more typically from 25:75, and preferably in a substantially equal amount.

Sections of the PE1-1, ZM1-1, ZM1-2 and MD3-4 were sequenced using standard techniques. The sequence obtained for the $V_H$ region of PE1-1 is given in Table 8-1, and areas corresponding to the CDR1, CDR2, and CDR3 ($D_H$ and $J_{H4}$) are noted. As the CDR regions are particularly important regions in determining the binding properties of an antibody, this invention includes an antibody that has an amino acid sequence of its CDR1 region which is substantially similar to that of PE1-1, as set forth in Table 8-1. This invention also includes an antibody that has an amino acid sequence in its CDR2 region which is substantially similar to that of PE1-1, as set forth in Table 8-1. Further, this invention also comprises an antibody that has an amino acid sequence of its CDR3 region which is substantially similar to the CDR3 region of PE1-1, as set forth in Table 8-1.

Likewise, the $V_H$ region of ZM1-1 was sequenced as is given in Table 8-2. Areas corresponding to its CDR1, CDR2, and CDR3 ($D_H$ and $J_{H4}$) are also indicated. This invention includes an antibody which has an amino acid sequence of its CDR1 region which is substantially similar to that of ZM1-1 as set forth in Table 8-2. Also, this invention includes an antibody which has an amino acid sequence of its CDR2 region which is substantially similar to that of ZM1-1 as set forth in Table 8-2, and further this invention also comprises an antibody that has an amino acid sequence of its CDR3 region which is substantially similar to that of ZM1-1 as set forth in Table 8-2.

The DNA sequences which code for the regions of ZM1-2 and MD3-4 are given in Table 8-3 and 8-4 respectively. This invention also includes any antibody which has amino acid sequences which are substantially similar to that of the regions of ZM1-2 and MD3-4 as set forth in Tables 8-3 and 8-4.

The DNA sequences which code for the $V_H$ regions of PE1-1, ZM1-1, ZM1-2 and MD3-4 were determined and appear in Tables 8-1 and 8-2, 8-3 and 8-4 respectively. These sequences or appropriate fragments may be used in cloning antibodies (or modified antibodies) or as probes. Antibodies which are produced through genetic engineering processes (rather than conventional harvesting from hybridomas) can be made using cloning techniques which are known in the art. DNA from other sources may be used to produce a synthetic antibody molecule which retains the binding characteristics of PE1-1, ZM1-1, ZM1-2 and MD3-4 by virtue of having substantially similar CDR1, CDR2, and/or CDR3 regions. Such antibodies are within the scope of this invention.

The DNA sequences which code for the $V_L$ light chain variable regions of PE1-1, ZM1-1, ZM1-2 and MD3-4 are given in Tables 9-1, 9-2, 9-3, and 9-4, respectively. This invention also includes any antibody which has amino acid sequences which are substantially similar to that of the regions of PE1-1, ZM1-1, ZM1-2 and MD3-4 as set forth in Tables 9-1, 9-2, 9-3 and 9-4.

Also within the scope of this invention are the DNA sequences which code for the $V_H$ region, the $V_L$ region, the CDR1 regions, the CDR2 regions and/or the CDR3 regions of PE1-1, ZM1-1, ZM1-2 and MD3-4. Also included is DNA which would hybridize to any of the aforementioned sequences under stringent hybridization conditions. This DNA is substantially free from other DNA of the donor mammal, and may contain introns or it may be cDNA.

As used throughout the specification and claims, the following definitions are intended. An amino acid sequence is "substantially similar" to another amino acid sequence if their amino acid homology is at least 80%. Referring to DNA, "stringent hybridization conditions" are those in which hybridization is effected at 60° C. in 2.5 X saline citrate buffer (SSC) followed merely by rinsing at 37° C. at a reduced buffer concentration which will not affect the hybridizations which take place. "Associated mammalian DNA" means DNA present in the mammal which is the source of the $V_H$ antibody chain, but which is not involved in coding for an antibody or antibody fragment.

The invention is more fully exemplified in the following non-limiting examples.

EXAMPLE 1

Production of Antibody Cell Lines

Human volunteers are immunized with hepatitis B vaccine. MD3-4, ZM1-2, ZM1-1, and PE1-1 hybridoma cell lines are derived from lymphocytes of individuals immunized with HEPTAVAX® vaccine (Merck & Co.). Cell line L03-3 is developed from cells of an individual injected several times with HEPTAVAX® vaccine, and just preceding the fusion, RECOMBIVAX® (Merck & Co.). Peripheral blood lymphocytes are purified by density gradient centrifugation on a cushion of Percoll (Pharmacia Inc.), density 1.085 g/ml. The isolated lymphocytes are washed three times in Hank's Balanced Salt Solution and mixed with an equal number of cells from (mouse×human) cell line SPAZ-4. The cell mixture is pelleted at room temperature with 400 × g for 5 minutes. After removing the medium, the cell pellet is treated with a 50% solution of PEG-1000 in Dulbecco's Minimal Essential Medium (MEM) for 1 minute at 37° C. after which the medium was slowly diluted with Dulbecco's MEM. The cells are collected by centrifugation and resuspended into Dulbecco's MEM containing 20% fetal bovine serums. The cells are seeded at approximately $2 \times 10^6$ cells per ml into microwell plates. On the following day fresh medium containing the components of HAT medium (hypoxanthine aminopterin thymidine) is added in order to select against non-fused SPAZ-4 cells. On day 4 after fusion the medium is replaced with fresh medium containing only HT as all cells sensitive to HAT-selection had been killed by that time.

After 3 to 4 weeks, when good growth of hybridoma-like cells could be seen microscopically, supernatants are tested for the presence of anti-hepatitis B surface antigen antibody. An ELISA-assay using a 1/100 dilution of HEPTAVAX® vaccine on the solid phase is used. After incubation with the supernatants the plates are developed with a VECTASTAIN® kit of biotinylated goat anti-human immunoglubulin and avidin-coupled horseradish peroxidase (Vector Laboratories Inc.). The enzyme is detected by the color reaction with phenylenediamine. Positive cultures are picked into new wells and a part of the cells is cloned by limiting dilution in Dulbecco's MEM containing 20% fetal bovine serum and $10^7$ mouse thymocytes per milliliter. The cloning plates are tested by the same ELISA method as described above and positive cultures are expanded and frozen.

All the cell lines behave as typical (mouse×human)× human hybridomas and produce their respective antibodies in concentrations ranging up to 25 mg/l in standard suspension culture.

EXAMPLE 2

Immunochemical Characterization

A. Antibody Class/Subclass

The immunoglobulin class of antibodies PE1-1, ZM1-1, ZM1-2, MD3-4 and L03-3 is determined using ELISA methodology. Each antibody is captured on an antigen-coated plate and each assay is developed with subclass specific, peroxidase-conjugated anti-human Ig (Tago). Each of the antibodies are clearly $IgG_1$.

B. Light Chain Type

Using ELISA methods similar to those described in A, above, each antibody is tested with anti-κ or anti-λ light chain reagents (Tago). The following results are obtained.

| | |
|---|---|
| PE1-1 | lambda |
| ZM1-1 | kappa |
| ZM1-2 | kappa |
| L03-3 | lambda |
| MD3-4 | lambda |

C. Isoelectric Focusing (IEF)

A sample of antibody L03-3 or PE1-1 is applied to gel. Each is found to behave as a basic protein.

D. Specificity

Purified HBsAg of subtypes adw and ayr are purchased from Scripps Laboratories, San Diego, Calif. HBsAg subtype ayw is obtained from Connaught Laboratories (Willowdale, Ontario). ELISA assays are performed essentially as described by Ostberg, et al. (1983) *Hybridoma* 2:361–367.

PE1-1 reacts with both ayr and adw, but it reacts slightly better with the adw subtype. L03-3 reacts substantially equally well with ayr and adw. ZM1-1 shows higher reactivity with adw, but ZM1-2 binds slightly better to ayr. These results are confirmed for PE1-1 and L03-3 by Scatchard analysis in solid phase RIA with solid adsorbed ayr or adw antigen. Thus, although these monoclonal antibodies apparently do not bind to the subtypic determinant, their reaction with HBsAg can be significantly affected by the subtype.

G. Allotype Determination

Allotypes are determined using reagents supplied by the Central Laboratory of the Netherlands Red Cross Transfusion Service. Inhibition ELISA or direct binding ELISA are used. Results are presented in Table 1, below. As can be seen, there is no apparent restriction on high affinity anti-HBSAg antibodies with respect to light chain or allotype.

TABLE 1

Allotypes of Anti-HBsAg Monoclonal Antibodies

| Antibody | Allotypes | | | |
|---|---|---|---|---|
| | a | f | z | Km(3) |
| PE1-1 | − | + | − | * |
| ZM1-2 | + | − | + | + |
| L03-3 | − | + | − | * |
| ZM1-1 | ND | ND | ND | + |

ND = Not determined
*Antibody has λ light chain which does not have Km allotypes G. Affinity The affinity for solid adsorbed HBsAg is determined for each antibody using radiolabelled antibodies essentially as described by Wands, et al. (1981) *Gastroenterology* 80:225–232, which is hereby incorporated by reference. Antibodies are labeled with $^{125}I$ with Iodogen (Pierce). For each monoclonal except L03-3, the solid phase absorbed HBsAg is ayw. L03-3 is assayed with both ayr and adw with essentially the same results. Antibody-antigen incubation occurs at room temperature.

The relative affinity is also determined using an inhibition ELISA in which varying concentrations of soluble HBsAg (ayw subtype) are pre-incubated with monoclonal antibody and the mixture is then incubated at 37° C. in a microtiter well coated with HBsAg. Results are presented below in Table 2.

TABLE 2

Affinity of Monoclonal Antibodies for HBsAg

| Antibody | Solid Phase RIA, $M^{-1}$ | Inhibition ELISA, $M^{-1}$ |
|---|---|---|
| PE1-1 | $3.6 \times 10^9$ | $\sim 2 \times 10^9$ |

TABLE 2-continued

| Affinity of Monoclonal Antibodies for HBsAg | | |
|---|---|---|
| Antibody | Solid Phase RIA, $M^{-1}$ | Inhibition ELISA, $M^{-1}$ |
| ZM1-2 | $1.5 \times 10^9$ | $\sim 7 \times 10^8$ |
| L03-3 | $1.7 \times 10^9$ | $\sim 1 \times 10^8$ |
| ZM1-1 | $5 \times 10^9$ | $\sim 1 \times 10^8$ |

As can be seen from the table above, for both PE1-1 and ZM1-2 the ELISA results are approximately two-fold lower than the RIA results, which is within the range of experimental error. A Scatchard plot of the results of the RIA performed on ZM1-1 indicates that there might be a low affinity binding site. It is thus possible that the ELISA is measuring this low affinity binding site, as the ELISA results are some 50-fold lower than the RIA. In addition, Scatchard plots also indicate that there are considerably less high affinity ZM1-1 sites than ZM1-2 or PE1-1 high affinity sites. While not wishing to be bound by theory, it appears that ZM1-1 may have the highest affinity for HBsAg of the four antibodies compared, but only for HBsAg in a certain spatial arrangement. This arrangement is only manifested in a small percentage of HBsAg molecules. It is also possible that this may be due to bivalent binding of ZM1-1 to HBsAg while the low affinity site is monovalent.

EXAMPLE 3

Potency of PE1-1

Antibody PE1-1 is tested for potency in the AUSAB radioimmunoassay (Abbott). Tests are performed against the Bureau of Biologics Reference Hepatitis B immune globin, and several commercial hepatitis B immune globulin preparations (H-Big Immune Globin®, Hep B Gammagee Immune Globin®, and Hyper Hep Immune Globin®, all purchased from a pharmaceutical supply house). Despite the fact that the immune globulin preparations are polyclonal and PE1-1 is monoclonal, the binding data are within the criteria of the Bureau of Biologics for comparing immune globulin preparations, i.e., the lines were parallel at a probability level less than or equal to 0.01.

Determination of potency is as follows. Preparations are compared on a weight basis (an absorbance at 208 nm of 1.4 is assumed equal to 1 mg/ml). Preparations of PE1-1 which have been stored at 5° C. are then compared with the above polyclonal preparations which have also been stored at 5° C. The logarithm of 1000 divided by µg/ml in the preparation (i.e. the log of a number that is inversely proportional to the concentration of the immunoglobin, similar to the log of the dilution factor) is then plotted vs. log counts per minute (average of triplicates). The hypothesis that the fitted lines are parallel is tested using analysis of variance. It is found that the lines are parallel at a probability level of less than or equal to 0.01. Lines of all preparations are parallel and a common slope is determined. The x-intercepts are calculated from the common slope and the difference in intercepts used to determine the difference in potency. By this procedure, monoclonal antibody PE1-1 is some 435 times more potent than the Bureau of Biologics reference hepatitis B immune globin. Since the commercial hepatitis B immune globulin preparations were found to be two-fold (or less) more potent than the Bureau of Biologics reference preparation, PE1-1 is at least 200 times more potent than the commercial hepatitis B immune globulin preparations on a weight basis.

EXAMPLE 4

A. Binding Kinetics

Direct binding enzyme linked immunoassays are used to compare the kinetics of binding to HBsAg of antibodies PE1-1 and ZM1-2. ELISA microtiter plates are coated with HEPTAVAX® vaccine at 1 µg/ml. Wells are then incubated at 37° C. with 2% fetal calf serum in phosphate buffered saline. Monoclonal antibody PE1-1 or ZM1-2 at 0.5 µg/ml in 2% fetal calf serum are incubated in the wells for various times. At the indicated times the antibody solution is removed and the well is rinsed three times with fresh 2% fetal calf serum. The well is then incubated with 2% fetal calf serum until the wells for the 90 minute time point contain 2% fetal calf serum. Thus, solution is then replaced with either peroxidase conjugated goat anti-lambda chain (PE1-1 wells) or goat anti-kappa chain (ZM1-2 wells). Quantitation of peroxidase conjugate bound to plastic is accomplished with the addition of O-phenylenediamine and $H_2O_2$. Results are presented in FIG. 1, where a single line is PE1-1 and a double line is ZM1-2.

As can be seen in FIG. 1, at a concentration at which PE1-1 is almost completely reacted in 5 minutes, the reaction of ZM1-2 with solid adsorbed HBsAg is not completed in 30 minutes and may continue to react for 90 minutes or more. Thus, PE1-1 binds significantly faster to antigen in this assay. Assuming this also occurs in vivo, PE1-1 is likely to be more efficient in neutralizing viral particles before they can infect the liver.

B. Relative Position of Epitopes

The relative position of the epitopes of antibodies PE1-1, L03-3, and ZM1-2 are determined. A simultaneous sandwich immunoassay with a solid-adsorbed monoclonal antibody is used. The same antibody is radiolabelled and incubated in a microtiter well with the inhibitor and serum from a hepatitis B positive patient. Radiolabelled PE1-1 Fab fragment is used while radiolabelled L03-3 is intact IgG. Results are presented in Table 3, below.

TABLE 3

| Inhibition of Binding of Radiolabelled Monoclonal Antibody to HBsAg by Unlabelled Monoclonal Antibodies | | | |
|---|---|---|---|
| Solid-Absorbed maB | Iodinated maB | Inhibitor maB | $IC_{50}$ ng/ml |
| L03-3 | L03-3 | L03-3 | 10 |
| L03-3 | L03-3 | PE1-1 | >22,500 |
| PE1-1 | PE1-1 | PE1-1 | 8 |
| PE1-1 | PE1-1 | ZM1-2 | 76 |
| PE1-1 | PE1-1 | L03-3 | >22,500 |

Monoclonal antibody ZM1-2 is only approximately nine times less effective in inhibiting $^{125}I$-PE1-1's binding to HBsAg than unlabelled PE1-1, whereas L03-3 is thousands of times less effective. Thus, the epitopes of ZM1-2 and PE1-1 are probably near each other on the HBsAg molecule while the L03-3 epitope is probably on a different part of the molecule. The reciprocal experiment, PE1-1 inhibition of radiolabelled L03-3, provides further evidence that PE1-1 and L03-3 bind to epitopes that are not overlapping.

The similarity of PE1-1 and ZM1-2 epitopes and their difference from the L03-3 is confirmed by immunoassay with reduced and alkylated HBsAg. L03-3 can bind to denatured antigen while both ZM1-2 and PE1-1 cannot so bind. It should be noted that PE1-1 and ZM1-2 have distinct epitopes since their reaction with different subtypes varies.

C. Pharmokinetics of PE1-1 in Rhesus Monkeys

Figure 2:
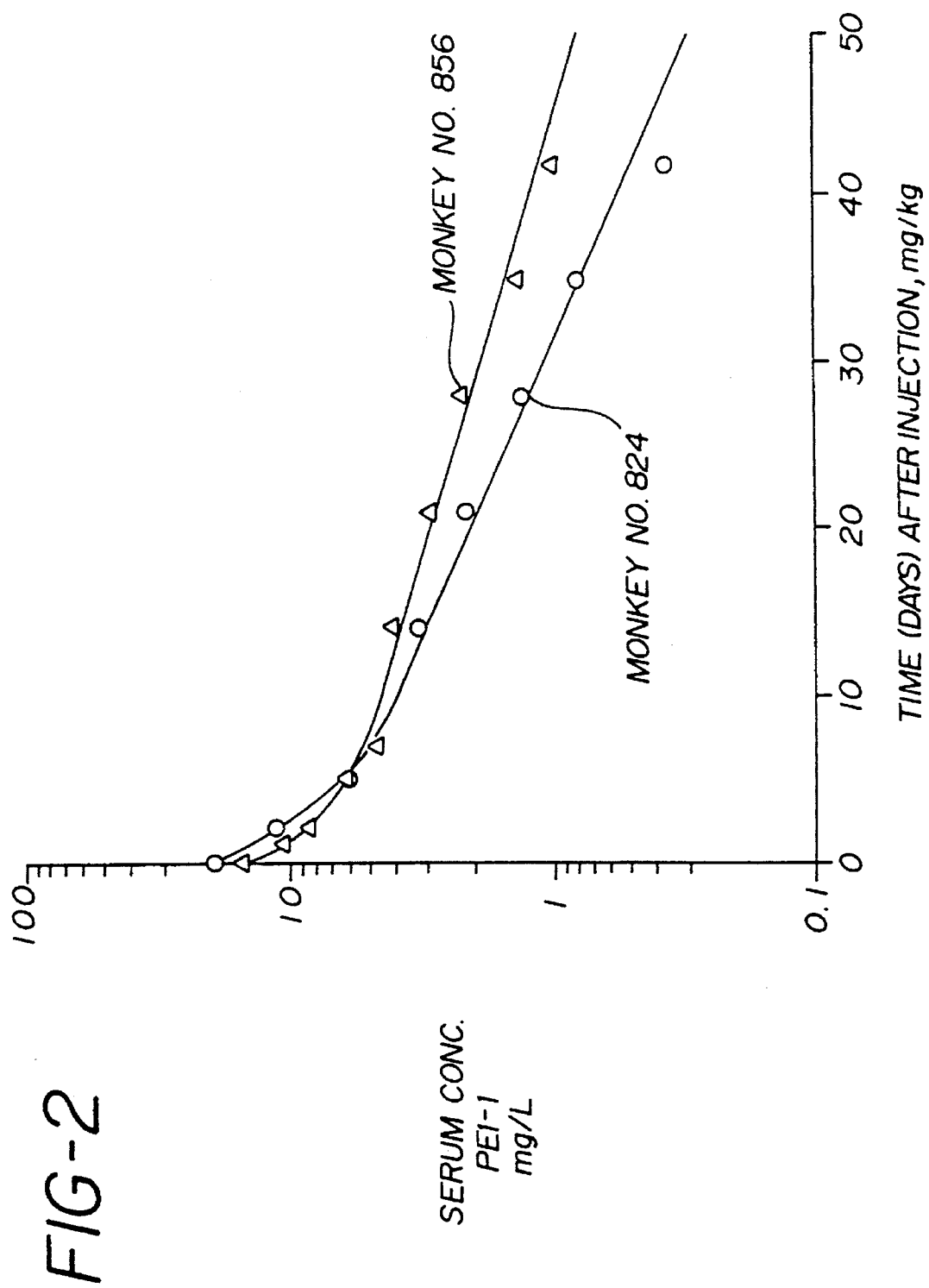
FIG. 2 shows the serum levels of antibody PE1-1 in rhesus monkey serum determined at various times post-dosage. Details are given in Example 4C.

The pharmokinetics of PE1-1 is studied in two rhesus monkeys. Each animal receives a single intravenous bolus injection (0.5 mg/kg) of monoclonal antibody PE1-1. Serum levels of PE1-1 are determined at various times post-dose using an ELISA based sandwich immunoassay with HEPTAVAX® vaccine coated on ELISA plates and rabbit anti-idiotypic antibodies to PE1-1. Results are shown in FIG. 2.

Serum levels of PE1-1 in the two rhesus monkeys are characterized by a biphasic decline (t $\frac{1}{2}\alpha=1$ and 1.4 days; t $\frac{1}{2}\beta=11$ and 16 days) with the shorter half-life possibly associated with the distribution phase of the monoclonal antibody. The volume of distribution at steady state (Vdss) is calculated to be 114–144% of the plasma volume, which suggests little distribution of PE1-1 to a tissue compartment in the antigen-free monkey.

EXAMPLE 5

Clinical Trials

A. Compassionate use of PE1-1 in Two Patients with End-stage Liver Disease Secondary to Chronic Active Hepatitis B and Hepatocellular Carcinoma Undergoing Liver Transplantation PE1-1 was provided on a compassionate need basis to two patients with end-stage liver disease undergoing liver transplantation. Patient #1 was a 56 year old male with a 20 year history of chronic active hepatitis and a diagnosis of hepatocellular carcinoma. The second patient was a 10 year old male thought to have been infected with hepatitis B at birth. Patient #2 was initially evaluated for a large mass in the right lobe of the liver, which a biopsy confirmed was hepatocellular carcinoma.

Preoperative doses of PE1-1 were administered to these patients and significantly reduced their circulating HBsAg levels before the transplant procedure. Each patient also received two 20 mg doses of PE1-1 during transplantation. Postoperative dosing then began on the second day following surgery.

Patient #1 never became HBsAg negative, although his circulating HBsAg levels did diminish markedly from their pretreatment level. Patient #2 became HBsAg negative, first noted on post-transplant day 9. Patient #1 received additional doses of PE1-1 ranging from 5–40 mg at 2–20 day intervals. Patient #2 received either 5 or 10 mg doses on average of every 21–28 days.

No adverse events were reported for either of these patients during the period they received PE1-1. However, approximately four weeks after Patient #1 was discharged from the hospital, it was determined that he had metastatic malignancy. He expired on post-transplant day 139. No evidence of recurrent hepatitis was noted during his post-transplant course despite the presence of detectable circulating HBsAg. Although a hepatitis B virus DNA assay was negative preoperatively, a single positive value was detected 60 days post-transplant.

On post transplant day 143, Patient #2 was first seen to be positive for HBsAg. The HBsAg level fluctuated for a short time before it then stabilized at a level signicantly below his pretreatment levels. Isolates of this patient's hepatitis B virus obtained before treatment with PE1-1 and at later times were analyzed for their binding ability to PE1-1. PE1-1 was found to be able to bind to the variant virus, but not as well as it had to the wild-type virus.

Genetic analysis of the two viral isolates indicated single nucleotide differences in a highly conserved region of the major viral surface protein. Such differences, when compared to the pre-treatment virus, could potentially encode for a single amino acid difference which would reduce the binding ability of PE1-1 to the hepatitis B viral binding particle.

B. Use of PE1-1 in Patients with Chronic Active Hepatitis B Undergoing Liver Transplantation (Not Complicated by Hepatocellular Carcinoma)

This study involved five patients who were HBsAg positive (but did not have hepatocellular carcinoma) and who underwent liver transplantation. Each patient was administered three daily preoperative doses of PE1-1, (10, 20 and 40 mg, respectively) over a three day period. The liver transplants were then performed from a minimum of two days to a maximum of 32 days following their preoperative dose of the study drug. An additional 40 mg dose of PE1-1 was administered during the operation. All five transplants were successfully completed.

The patients' HBsAg titers, liver enzymes, and other clinical parameters were closely monitored during their hospital stays. Follow-up evaluations and administration of PE1-1 by each patients' private physician continued on a regular basis (approximately every 1 to 3 weeks). Dosing and other parameters varied from patient to patient.

Two patients (#5 and #6) had similar results to Patient #2, above, in that a variant virus appeared after a period of negative HBsAg screening results. The sera of these patients remained active with PE1-1. Sequence analysis indicated the presence of single nucleotide differences between the variants in the patients' sera and wild type virus. Two variants were detected in each patient. Immunoassays and sequence analysis indicated that the variants in each patient were different and they also differed from the variants of Patient #2.

Patient #3 is a 39 year old Caucasian male who had end-stage liver disease secondary to a 16 year history of chronic hepatitis B. The three preoperative doses of PE1-1 that were administered to Patient #3 caused a substantial reduction in his HBsAg titer. On post-transplant days 2 and 3, he received 20 mg of PE1-1 and was first noted to be HBsAg negative on post-transplant day 2. For two months thereafter, Patient #3 received 10 mg PE1-1 on an average of every 1 to 7 days. Since then, he has received 7.5 or 10 mg doses of PE1-1 every 14 to 43 days. Histopathological evaluation of a liver biopsy performed in February, 1989 was negative for both HBsAg and HBcAg. Patient #3 remains HBsAg negative 582 days after transplant. In addition to receiving PE1-1, he has also received three consecutive monthly injections of RECOMBIVAX® in July, August and September, 1989.

Patient #4 was a 40 year old Arabic female who had end-stage liver disease secondary to a 10+ year history of chronic active Hepatitis B. The three preoperative doses of PE1-1 given to Patient #4 caused a substantial reduction in her HBsAg level. Patient #4 received 20 mg of PE1-1 on post-transplant days 1 and 2, and was found to be HBsAg negative on post-transplant day 6. For two months thereafter, she received 10 mg PE1-1 on average of every 3 to 8 days. Since then, she received 10 mg PE1-1 every 5 to 26 days. Approximately 1 year after her transplant, the patient developed hepatic artery thrombosis, but remained HBsAg negative, and was re-transplanted. Three days later, due to ischemia, a third transplant was performed. Twenty days following, a fourth transplant was performed due to infection. The patient expired 18 days after the fourth transplant (404 days after her initial transplant), secondary to liver failure and bacterial sepsis. Histopathological evaluation of a liver biopsy from her first transplanted liver showed that she was HBsAg negative.

Patient #5 is a 38 year old Caucasian male who had end-stage liver disease secondary to chronic active hepatitis B. The preoperative doses of PE1-1 administered to the patient substantially lowered his circulating HBsAg level. Patient #5 received 20 mg PE1-1 on post-transplant days 2 and 3, and was found to be HBsAg negative on post-transplant day 3. During the first two months post-transplant, he received 10 mg PE1-1 on average of every 3–7 days. Later, he received 10 mg PE1-1 every 9 to 26 days. The patient was noted to be HBsAg positive on post-transplant day 252, although his antigen level is substantially lower than his pre-transplant level. Histopathological evaluation of a liver biopsy performed in January 1990 is positive for HBsAg and HBcAg.

Patient #6 is a 38 year old Caucasian male who had end-stage liver disease secondary to chronic active hepatitis B and alcohol abuse. This patient acquired his initial infection via a blood transfusion. Prior to the transplant, he was positive for both HBsAg and HBeAg. Each preoperative dose of PE1-1 caused a decrease in the level of the patient's HBsAg titer. Patient #6 received 20 mg of PE1-1 on post-transplant days 1 and 2 and was noted to be HBsAg negative on post-transplant day 1. For two months thereafter, Patient #6 received 10 mg of PE1-1 on average of every 3–14 days. Subsequently he has received 10 mg PE1-1 every 7 to 63 days on an outpatient basis. The first HBsAg positive response was noted on post-transplant day 251 and occurred after his longest duration (63 days) between doses of PE1-1. Although at present Patient #6 is positive for HBsAg, his titer remains significantly lower than pre-transplant levels.

Patient #7 is a 38 year old Caucasian female with a history of IV drug abuse. This patient had end-stage liver disease secondary to chronic active hepatitis B. Prior to transplantation, the patient was positive for HBsAg and HBeAg. Each preoperative dose of PE1-1 caused a decrease in the patient's HBsAg titer. The first month post-transplant, Patient #7 received between 10 and 40 mg of PE1-1 on the average of every 1–7 days, and was noted to be HBsAg negative on post-transplant day 16. Subsequently, she received 10 mg PE1-1 every 15 to 29 days. Histopathological evaluation of a liver biopsy performed in July, 1989 was negative for HBsAg and HBcAg. Patient #7 remains HBsAg negative 464 days post-transplant.

EXAMPLE 6

Reactivity with Variant Virusus

The reactivity of the monoclonal antibodies PE1-1, ZM1-2, and LO3-3 with variant hepatitis B viruses isolated from patients described in Example 5 is investigated. Radioimmunoassays are performed by determining the radioactivity bound to a solid phase adsorbed-antibody. A solution of a monoclonal antibody at a concentration of 20 μg/ml in phosphate-buffered saline containing 0.02% $NaN_3$ is incubated for at least 18 hours in U-bottom wells (Falcon MicroTest III Flexible Assay Plates). The solution is removed from the wells and the wells are then washed three times with distilled water. Fetal calf serum at a concentration of 2% in phosphate-buffered saline is added and incubated overnight at room temperature with solutions of serum HBsAg or controls and $^{125}I$-radiolabelled antibody (approximately 4,000 cpm in 1% fetal calf serum). Wells are then washed with distilled water three times. Individual wells are excited and counted. Results are presented in Table 4, below.

TABLE 4

Relative Reactivity of Serum-Derived Variant HBsAg with HBsAg-Specific Monoclonal Antibodies

| Sample* | LO3-3:LO3-3** | PE1-1:ZM1-2 | ZM1-2:ZM1-2 |
|---|---|---|---|
| Control | 1.000 | 1.000 | 1.000 |
| Patient #2 (234) | 0.013 | 0.070 | 0.233 |
| Patient #4 (251) | 0.007 | 0.024 | 0.010 |
| Patient #3 (264) | 0.043 | 0.173 | 0.179 |

*Representative HBsAg-positive serum samples derived from patients after liver transplantation and treatment with an anti-HBsAg therapeutic monoclonal antibody PE1-1. Numbers in parentheses denote days after transplantation.
**LO3-3:LO3-3 indicates a radioimmunoassay composed of both solid-adsorbed and radiolabelled human monoclonal antibody LO3-3. PE1-1:ZM1-2 indicates a radioimmunoassay composed of human monoclonal antibody PE1-1 solid-adsorbed and human monoclonal antibody ZM1-2 radiolabelled. ZM1-2:ZM1-2 indicates a radioimmunoassay composed of both solid-adsorbed and radiolabelled human monoclonal antibody ZM1-2. Control HBsAg-positive serum reacted well with antibodies LO3-3, PE1-1 and ZM1-2.

EXAMPLE 7

Large Scale Production of Antibodies

To initiate a production run with cells, one or more ampule(s) of frozen cells is removed from liquid nitrogen. After rapidly heating in a 37° C. water bath until most of the ice has melted, the ampule is opened inside a vertical laminar flow hood. The contents of the ampule are mixed with a 1 ml volume of Dulbecco's MEM/Ham's F12(1:1) (DMEM/F12) to which ferric salts have been added to a final concentration of 50 μM of $Fe^{+++}$. After mixing, the tube is filled up to approximately 10 ml with the same medium and the cells are collected by centrifugation. The cell pellet is resuspended into 5 ml of the above mentioned medium with 20% fetal bovine serum and seeded into 1 well of a 6-well tissue culture plate. The cells are incubated in a 37° C. incubator in a 5% $CO_2$-atmosphere. When the cells have established themselves in culture and start to multiply and have an approximate cell concentration of $10^6$/ml, the cells and the medium are moved into a tissue culture flask with a surface area of 80 $cm^2$ and diluted to 40 ml using DMEM/F12 (without serum). When the cells have once again reached a concentration of $10^6$/ml, they, and the medium, are moved into a tissue culture flask with a surface area of 175 $cm^2$ and further diluted to a volume of 100 ml using DMEM/F12. When the cells have once again reached optimal concentration, the cells and the medium are transferred into a roller bottle with a 850 $cm^2$ surface area and diluted to a final volume of 500 ml. When this roller bottle has reached optimal cell concentration, it is split ⅓ into new roller bottles using the same medium as before. This splitting process of the roller bottles is continued until a sufficient number of bottles have been obtained in order to give a desired number of cells to seed into the Verax System 200 reactor.

The Verax System 200

The Verax System 200 reactor is a closed cell culture system where cells are cultivated in stainless steel weighted microspheres (density 1.6 g/mL) composed of cross-lined type I bovine collagen. The microspheres are loaded into a vertical transparent glass tube through which the culture medium (same as above) is pumped, entering at the bottom. The inlet to the tube is formed in such a fashion that the microspheres will establish a fluidized bed configuration when the medium is pumped through at a suitable velocity. During operation, fresh medium is constantly added and conditioned medium removed at a rate determined by the cell growth as monitored by glucose consumption. Temperature is maintained at 37° C.; pH is maintained at 7.1 and oxygen/nitrogen ratio is also controlled.

After loading of the microspheres in 1% fetal bovine serum containing medium, the reactor is run for at least three days without cells to ascertain that the microsphere loading did not contaminate the System. During this time the reactor is fed with protein-free medium to reduce the priming dose of fetal bovine serum. If all systems are operating satisfactorily, the cells from the roller bottles are inoculated into the reactor.

The Verax System 2000

This equipment uses the same type of microspheres as the System 200, and its controls and operations are essentially the same as for the smaller system. The System 2000 represents an approximately 15-fold scale-up compared to the System 200.

Monitoring of Yield of Antibody from Full-Scale Culture

The conditioned medium is monitored, each time the harvest tank is emptied, for the level of human immunoglobulin in the supernatant using an ELISA-type assay. The results are confirmed using a Protein A HPLC method.

Harvesting of Cell Culture Media and Production of Harvest Pool

The conditioned medium is continuously being removed from the Verax equipment into a refrigerated harvest tank. This medium is later unloaded (using the nitrogen pressure in the verax system) into a mobile stainless steel tank for further processing.

Cell Culture Media

The media routinely used is a 1:1 mixture of Dulbecco's MEM H21 and Ham's F12 (Mediatech). The medium is purchased as a powder sufficient for 50 liters of finished medium. Two such containers of each medium powder are added into a stainless steel tank containing approximately 190 liters of water. The powder is suspended with an impeller until all has been dissolved. Sodium bicarbonate is added as recommended by the manufacturer and the pH of the medium is set to 7.4. Sodium selenite is added to a final concentration of 17.3 µg/l and the volume is topped up to 200l with water. The medium is also supplemented with ferric ions in the form of ferric nitrate/sodium citrate to a final concentration of 50 µM Fe+++. The medium is immediately added to the medium tank of the Verax System S200 through the built-in sterilization filter. No protein is added to the medium. No antibiotics of any type are ever used.

PURIFICATION OF THE MONOCLONAL ANTIBODY

Description of Methodology of Harvesting and Purification of End Product

The monoclonal antibody is produced in cell culture from a hybridoma cell line in the absence of serum. This means that we have a need to remove from the final product only components from the cellular material. As human monoclonal antibodies are not in themselves expected to be immunogenic, it becomes very important to remove all potentially immunogenic components.

The goal of the purification procedures is a final product that is more than 99.9% pure, using affinity chromatography. We depend heavily on the biological specificity of affinity chromatography. Each step of the purification process (summarized in Table 5) is discussed in more detail, supra.

TABLE 5

| Step | Purification Summary | |
|---|---|---|
| | Conditions | Materials |
| Cell Removal | Room Temp. | Polyvinylidene difluoride filters, 0.65/0.45 µm absolute. |
| Concentration | | |
| Microfiltration | 4° C. | Polysulfone filter nominal 30,000 daltons. Polyester (0.8 µm) and cellulose acetate (0.2 µm) absolute filters. |
| Protein A chromatography | 4° C. | Agarose coupled *Staphyloccocus aureus* Protein A. |
| Concentration | 4° C. | Cellulose triacetate filter, nominal 20,000 dalton. |
| Gel chromatography. | 4° C. | Sephacryl S-300, Ringer's Lactated Solution |
| Ion exchange | 4° C. | Sephacryl S-300, Ringer's Lactated Solution |

Cell Harvest and Removal of Particulate Materials from the Conditioned Medium Even though most of the cells are retained by the microspheres, a sizable number of cells are present in the harvested supernatant. To avoid gross contamination of the medium by cell components the supernatant is filtered through a polyvinylidene difluoride 0.65 µm Prostack® filter (Millipore), immediately after removal from the Verax harvest tank. This type of filter unit works in a tangential flow mode which allows filtration of large amount of particulate material without clogging the filter. The cleared medium is collected into a refrigerated stainless steel tank.

Concentration of Conditioned Medium

The conditioned medium is concentrated using a nominal 30,000 dalton polysulfone spiral wound membrane supplied by Millipore. After concentration, the pH is set to 7.0 using 1M acetic acid. The material is sterile filtered through a Sartobran-PH 0.8/0.2 µm (Sartorius) filter (the 0.8 µm component is polyester, the 0.2 µm component is cellulose acetate) before being stored at 4° C. The material is microfiltrated (0.22 µM Millipore) and filled into polypropylene vessels.

Protein A Chromatography

The extremely powerful purification step utilizes the high affinity of the human IgG1 antibody to *Staphylococcus aureus* Protein A.

The Protein A is purchased already coupled covalently by an amide bond to agarose. After packing the gel in a column, the column with its contents and attached tubing is sanitized by treatment with 70% ethanol in water for 24 hours. The column is then equilibrated with PBS, pH 7.0.

Performing the affinity chromatography separation on the Protein A column involves the following sequential steps:

A) Loading.

The concentrated conditioned medium is loaded on the column with a pump. The effluent from the column is collected and monitored for the presence of antibody by the human immunoglobulin ELISA. The column is loaded to such a degree that a measurable amount of antibody-containing fluid passes through the column. The overload fraction is separately recovered and recycled if it contains more than 20 mg/ml antibody.

B) Washing.

To remove unbound materials the column is extensively washed with phosphate buffered saline, pH 7 with sodium chloride added to a final concentration of 0.5M. This wash is followed by a second washing step using a buffer of 0.02M sodium citrate, pH 5.6, containing 0.5M sodium chloride. This wash releases small amounts of the human antibody.

C) Elution.

The bound monoclonal antibodies are eluted from the column using a buffer composed of 0.02M sodium citrate, pH 3.0, containing 0.5M sodium chloride. The eluted material is continuously diluted into a volume of 1M Tris-HCl, pH 8.0 to rapidly restore near-neutral conditions.

The Protein A purification is performed in a closed system utilizing a Waters 650 Protein Purification System.

Concentration of Protein A Column Eluate

In order to make the following purification step more effective and convenient, the eluate from the Protein A column is concentrated to at least 5 mg/ml antibody. The concentrate is sterile filtered through a 0.2 μm filter and the sterile concentrate is stored at 4° C. until sufficient materials have been collected for the next purification step.

Size Separation by Gel Chromatography on Sephacryl S-300 High Resolution

The antibody preparation is run on a Sephacryl S300 High Resolution (Pharmacia) gel, packed in a Pharmacia BP113/120 column with a bed volume of approximately 10 liters. The column is packed in Lactated Ringer's Irrigation USP (Travenol Laboratories). The elution of the column is monitored by a Waters 650 Protein Purification System.

The purpose of this step is not principally additional purification, but buffer change. After the elution of the Protein A column the antibodies are in a complex, hypertonic buffer composed of sodium citrate, sodium chloride and Tris-HCl. This buffer mixture can not be used directly as a vehicle for an intravenous injection. The buffer after this step is suitable both for intravenous injection and for long term refrigerated storage.

Removal of Host Cell DNA by Passage over an Ion Exchange Column

Even after the Protein A chromatography, which removes the bulk of DNA present in the concentrated supernatant, and the Sephacryl S-300HR which removes DNA molecules that are either significantly larger or significantly smaller than the monoclonal antibody product, there is a small, but detectable, presence of DNA in the antibody preparation. We have selected to remove this contaminant by an ion exchange step on a strong anion exchanger, Q Sepharose (Pharmacia Inc.). At the pH of Lactated Ringer's solution, antibody proteins have a positive charge, and are repelled by the anion exchanger. Nucleic acids, however, have a negative charge at this pH, and will bind to the column.

The column was packed according to the manufacturer's suggestions. After decanting the 20% ethanol solution the gel is delivered in, 100 ml of gel was suspended in 200 ml of Lactated Ringer's solution. The slurry is poured into a Pharmacia K50/30 column, and when the gel has packed itself to a constant volume, it is sanitized with 1 column volume of 0.5N sodium hydroxide, followed by 3 column volumes of Dulbecco's PBS, followed by 5 column volumes of Lactated Ringer's solution. Immediately prior to use the column was washed with an additional 5 column volumes of Lactated Ringer's solution. The sample is then passed through the column and the pass-through is collected in a sterile container.

EXAMPLE 8

Molecular Analyses of PE1-1, ZM1-1, ZM1-2 and MD3-4

The heavy variable ($V_H$) chain of antibodies PE1-1, ZM1-1, ZM1-2 and MD3-4 are isolated and sequenced. Total RNA is extracted from $10^7$ hybridoma cells of each cell line using procedures described in Sanz, et al. 1989 *J. Immunol.* 142:883, which is hereby incorporated by reference. Single stranded DNA is synthesized using AMV-reverse transcriptase as the enzyme and oligo-dT as the primer. The quantity of the synthesized ss-cDNA is assessed by measuring the incorporation of $^{32}$p-dCTP Polymerase chain reactions (PCR) are performed essentially as recommended by the manufacturer (Perkin Elmer Cetus, Norwalk, Conn.). One microgram of DNA is added to a 200 μm solution of each of dATP, dCTP, dGTP and dTTP, with 100 p moles each of primer and 5 units of Taq DNA polymerase. PCR cycles are as follows: denaturation at 98° C. for 3 minutes, annealing at 55° C. for 2 minutes, and extension at 72° C. for three minutes, controlled in a DNA thermal cycler (Perkin Elmer Cetus).

Amplified DNA is size selected on a 1.0% low melting agarose gel, ligated into the EcoRV site of a BLUESCRIPT phagemid vector, and transformed into $CaCl_2$ competent BSJ72 bacteria. Single stranded DNA for sequencing is isolated from each positive clone after superinfection with M13K07 as described by Sanz, et al., supra. Sequencing is accomplished via the dideoxy chain termination method as described by Sanger, et al. 1980 *J. Mol. Biol.* 143:161, except a modified T7 DNA polymerase (Sequenase) is used as described by Tabor, et al. 1987. *PNAS* (USA) 84:4767. Results are given in Tables 8-1, 8-2, 8-3 and 8-4.

TABLE 8-1

DNA sequence of the $V_H$ region of PE1-1 is shown below (SEQ ID NO: 1). The leader, $V_H$III, D, and $J_H$4 regions are denoted by the dashed line; complementarity-determining regions CDR1 and CDR2 are indicated by the asterisks. Amino acids appear as single letter abbreviations below the DNA (SEQ ID NO: 2).

```
<----------------------------LEADER----------------------------------------------------->  <--------\-
ATG GAG TTT GGG CTG AGC TGG GTT TTC CTC GTT GCT CTT TTA AGA GGT GTC CAG TGT CAG GTG
 M   E   F   G   L   S   W   V   F   L   V   A   L   L   R   G   V   Q   C   Q   V

\-------------------------------V_HIII----------------------------------------------------\-
CAG CTG GTG GAG TCT GGG GGA GGC GTG GTC CAG CTT GGG AGG TCC CTG AGA CTC TCC TGT GCA
 Q   L   V   E   S   G   G   G   V   V   Q   P   G   R   S   L   R   L   S   C   A

\-----------------------*******CDR1********-----------------------------------------------\-
GCC TCT GGA TTC ACC TTC AGT AGG TAT GGC ATG CAC TGG GTC CGC CAG GCT CCA GGC AAG GGG
 A   S   G   F   T   F   S   R   Y   G   M   H   W   V   R   Q   A   P   G   K   G

\-----------------*********************************CDR2***********************************\-
CTG GAG TGG GTG GCA GTG ATA TCA TAT GAT GGA AGT AAT AAA TGG TAT GCA GAC TCC GTG AAG
 L   E   W   V   A   V   I   S   Y   D   G   S   N   K   W   Y   A   D   S   V   K

\-***-------------------------------------------------------------------------------------\-
GGC CGA TTC ACC ATC TCC AGA GAC AAT TCC AAG AAC ACT CTG TTT CTG CAA ATG CAC AGC CTG
 G   R   F   T   I   S   R   D   N   S   K   N   T   L   F   L   Q   M   H   S   L

\----------------------------------------------------------------->  <--------D----------\-
AGA GCT GCG GAC ACG GGT GTA TAT TAC TGT GCG AAA GAT CAA CTT TAC TTT GGT TCG CAG AGT
 R   A   A   D   T   G   V   Y   Y   C   A   K   D   Q   L   Y   F   G   S   Q   S

\--------------->  <----------------------J_H4------------------->
CCC GGG CAC TAC TGG GTC CAG GGA ACC CTG GTC ACC GTC TCC TCA
 P   G   H   Y   W   V   Q   G   T   L   V   T   V   S   S
```

TABLE 8-2

DNA sequence of the $V_H$ region of ZM1-1 is shown below (SEQ ID NO: 3). The leader, $V_H$III, D, and $J_H$4 regions are denoted by the dashed line; complementarity-determining regions CDR1 and CDR2 are indicated by the asterisks. Amino acids appear as single letter abbreviations below the DNA (SEQ ID NO: 4).

```
<----------------------------LEADER----------------------------------------------------->  <--------\-
ATG GAG TTT GGG CTG AGC TGG GTT TTC CTT GTT GCT ATA TTA GAA GGT GTC CAG TGT GAG GTG
 M   E   F   G   L   S   W   V   F   L   V   A   I   L   E   G   V   Q   C   E   V

\-------------------------------V_HIII----------------------------------------------------\-
CAG CTG GTG GAG TCT GGG GGA GGT TTG GTA CAG CCT GGG GGG TCC CTG AGA CTC TCC TGT GCA
 Q   L   V   E   S   G   G   G   L   V   Q   P   G   G   S   L   R   L   S   C   A

\-----------------------*******CDR1********-----------------------------------------------\-
GCC TCT GGA TTC ACC TTC AGT AGG TAC GAC ATG TAC TGG GTC CGC CAA GCT ACA GGA AAA GGT
 A   S   G   F   T   F   S   R   Y   D   M   Y   W   V   R   Q   A   T   G   K   G

\-----------------*********************************CDR2***********************************\-
CTG GAG TGG GTC TCA GCT ATT GGT CCT ACT GGT GAC ACA TAC TAT GCA GAC TCC GTG AAG GGC
 L   E   W   V   S   A   I   G   P   T   G   D   T   Y   Y   A   D   S   V   K   G

\-----------------------------------------------------------------------------------------\-
CGA TTC ACC ATC TCC AGA GAA AAT GCC AAG AAC TCC TTG TAT CTT ACA ATG AAC GGC CTG AGA
 R   F   T   I   S   R   E   N   A   K   N   S   L   Y   L   T   M   N   G   L   R

\---------------------------------->  <------D------>  <------------------J_H4-\-
GCC GGG GAC ACG GCT GTG TAT TAC TGT GCA AGA GAT TTA GAA CTC TGG GGC CAG GGA ACC CTG
 A   G   D   T   A   V   Y   Y   C   A   R   D   L   E   L   W   G   Q   G   T   L
```

TABLE 8-2-continued

DNA sequence of the $V_H$ region of ZM1-1 is shown below (SEQ ID NO: 3). The leader, $V_H$III, D, and $J_H4$ regions are denoted by the dashed line; complementarity-determining regions CDR1 and CDR2 are indicated by the asterisks. Amino acids appear as single letter abbreviations below the DNA (SEQ ID NO: 4).

```
\--------------------->
GTC ACC GTC TCC TCA
 V   T   V   S   S
```

TABLE 8-3

DNA sequence of the $V_H$ region of ZM1-2 is shown below (SEQ ID NO: 5). The leader, $V_H$IV, D, and $J_H4$ regions are denoted by the dashed line; complementarity-determining regions CDR1 and CDR2 are indicated by the asterisks. Amino acids appear as single letter abbreviations below the DNA (SEQ ID NO: 6).

```
<----------------------LEADER----------------------------------------------------->  <--------\
ATG AAA CAC CTG TGG TTC TTC CTC CTG CTG GTG GCS GTT CCC AGA TGG GTC GTG TCC CAG GTG
 M   K   H   L   W   F   F   L   L   L   V   A   V   P   R   W   V   V   S   Q   V

\-----------------------V_H IV----------------------------------------------------------------\
CAG CTG CAG GAG TCG GGC CCA GGA CTG GTG AAG GCT GCG GAG ACC CTG TCC CTC ACC TGC ACT
 Q   L   Q   E   S   G   P   G   L   V   K   A   S   E   T   L   S   L   T   C   T

\----------------------*******CDR1********--------------------------------------------------\
GTC TCC CGT GGC TCC TTC AGT GAT TAC TTC TGG AAT TGG TTC CGG CAG CCC GCC GGG AAG CGC
 V   S   R   G   S   F   S   D   Y   F   W   N   W   F   R   Q   P   A   G   K   R

\-------------------*********************************CDR2***********************************\
CTG GAG TGG CTT GGG CGT GTC TAT ACC AGT GGA AGT GTC GAC TAC AAC CCC TCC CTC AAG AGT
 L   E   W   L   G   R   V   Y   T   S   G   S   V   D   Y   N   P   S   L   K   S

CGA GTC ACC GTG TCA GTG GAC ACG TCC AAG AAG CAG TTC TCC CTG AGG CTG AGC TCT GTG ACC
 R   V   T   V   S   V   D   T   S   K   K   Q   F   S   L   R   L   S   S   V   T

\------------------------------------------->  <------ D ------>  <---------------- J_H4--\
GTC GCG GAC ACG GCC GTG TAT TAT TGT GCG AGA GGA CTG TCC GGT TTT GAC TAC TGG GGC CAG
 V   A   D   T   A   V   Y   Y   C   A   R   G   L   S   G   F   D   Y   W   G   Q

\--------------------------------------->
GGA GCC CTG GTC ACC GTC TCC CCA
 G   A   L   V   T   V   S   P
```

TABLE 8-4

DNA sequence of the $V_H$ region of MD3-4 is shown below (SEQ ID NO: 7). The leader, $V_H$V, D, and $J_H3$ regions are denoted by the dashed line; complementarity-determining regions CDR1 and CDR2 are indicated by the asterisks. Amino acids appear as single letter abbreviations below the DNA (SEQ ID NO: 8).

```
<----------------------LEADER------------------------------------------------------> <--------\
ATG GGG TCA ACC GCC ATC CTT GGC CTC CTC CTG GCT GTT CTC CAA GGA GTC TGT GCC GAA GTG
 M   G   S   T   A   I   L   G   L   L   L   A   V   L   Q   G   V   C   A   E   V

\-----------------------V_H V----------------------------------------------------------------\
CAG CTG GTG CAA TCT GGA GCA GAG GTG AAA AAG CCC GGG GAG TCT CTG AGG ATC TCC TGT AAG
 Q   L   V   Q   S   G   A   E   V   K   K   P   G   E   S   L   R   I   S   C   K

\----------------------*******CDR1********--------------------------------------------------\
GGT TCT GGA TAC AGC TTT ACC AGC TAC TGG ATC AGC TGG GTG CGC CAG ATG CCC GGG AA  GGC
 G   S   G   Y   S   F   T   S   Y   W   I   S   W   V   R   Q   M   P   G   K   G

\-------------------*************************CDR2******************************************\
CTG GAG TGG ATG GGG AGG CTT GAT CCT AGT GCC TCC TCT GCC ATC TTC AGC CCG TCC CTC CAA
```

TABLE 8-4-continued

DNA sequence of the V_H region of MD3-4 is shown below (SEQ ID NO: 7). The leader, V_HV, D, and J_H3 regions are denoted by the dashed line; complementarity-determining regions CDR1 and CDR2 are indicated by the asterisks. Amino acids appear as single letter abbreviations below the DNA (SEQ ID NO: 8).

| L | E | W | M | G | R | L | D | P | S | A | S | S | A | I | F | S | P | S | L | Q |
|---|---|---|---|---|---|---|---|---|---|---|---|---|---|---|---|---|---|---|---|---|

\-***------------------------------------------------------------------------------------------------\-

| GGC | CAC | GTC | ACC | ATC | TCA | GTT | GAC | AAG | TCC | ATG | AGG | ACT | GCC | TAC | GTG | CAG | TGG | AGA | AGC | CTG |
| G | H | V | T | I | S | V | D | K | S | M | R | T | A | Y | V | Q | W | R | S | L |

\-----------------------------------------------> <------------------------------------ D --------\-

| AAG | GCC | TCG | GAC | ACC | GCC | ATG | TAT | TAC | TGT | GCG | AGA | CAT | GTC | CGC | GAA | AAG | AGT | ATG | GTT | CAG |
| K | A | S | D | T | A | M | Y | Y | C | A | R | H | V | R | E | K | S | M | V | Q |

\-------------------------> <------------------------------- J_H3 ------------------------------->

| GGA | GTC | ATT | ATA | AAG | GAC | GCT | TTT | GAT | ATC | TGG | GGC | CAA | GGG | ACA | ATG | GTC | ACC | GTC | TCT | TCA |
| G | V | I | I | K | D | A | F | D | I | W | G | Q | G | T | M | V | T | V | S | S |

EXAMPLE 9

Following the procedures of Example 8, the light variable (V_L) chain of antibodies PE1-1, ZM1-1, ZM1-2 and MD3-4 are isolated and sequenced. Results are given in Tables 9-1, 9-2, 9-3 and 9-4.

TABLE 9-1

DNA sequence of the V_L region of PE1-1 is shown below (SEQ ID NO: 9). The leader, VV and J3 regions are denoted by the dashed line; complementarity-determining regions CDR1, CDR2 and CDR3 are indicated by the asterisks. Amino acids appear as single letter abbreviations below the DNA (SEQ ID NO: 10).

<------------------------- V_lV ------------------------------------------------------------------\-

| CAG | TCT | CAG | CTG | ACG | CAG | CCG | CCC | TCG | GTG | TCA | GTG | GCC | CCA | GGG | CAG | ACG | GCC | AGG | ATT | ACC |
| Q | S | Q | L | T | Q | P | P | S | V | S | V | A | P | G | Q | T | A | R | I | T |

\----------************* CDR1 ****************--------------------------------------------\-

| TGT | GGG | GGA | GAC | ACC | ATT | GGG | AGT | AAA | AGT | GTG | AAC | TGG | TTC | CAG | CAG | AAG | CCA | GGC | CAG | GCC |
| C | G | G | D | N | I | G | S | K | S | V | N | W | F | Q | Q | K | P | G | Q | A |

\------------------------------- ********* CDR2 **********-------------------------------\-

| CCT | GTC | CTG | GTC | GTC | TAT | GAT | GAT | AAC | GAA | CGG | CCC | TCA | GGC | ATT | TCT | GAG | CGA | TTC | TCT | GGC |
| P | V | L | V | V | Y | D | D | N | E | R | P | S | G | I | S | E | R | F | S | G |

\---------------------------------------------------------------------------------------------\-

| TCC | AAC | TCT | GGG | AAC | ACG | GCC | ACC | CTG | ACC | ATC | AGC | AGG | GTC | GAA | GCC | GGG | GAT | GAG | GCC | GAC |
| S | N | S | G | N | T | A | T | L | T | I | S | R | V | E | A | G | D | E | A | D |

\--------------------------********* CDR3 *****> <***-------------------- J_l3 ------\-

| TAT | TAC | TGT | CAG | GTG | TGG | GAT | AGT | AGT | AGT | GAT | CAT | GTG | GTA | TTC | GGC | GGA | GGG | ACC | AAG | CTG |
| Y | Y | C | Q | V | W | D | S | S | S | D | H | V | V | F | G | G | G | T | K | L |

\--------------->

| ACC | GTC | CTA |
| T | V | L |

TABLE 9-2

DNA sequence of the V$_L$ region of ZM1-1 is shown below (SEQ ID NO: 11). The leader, VII and J5 regions are denoted by the dashed line; complementarity-determining regions CDR1, CDR2 and CDR3 are indicated by the asterisks. Amino acids appear as single letter abbreviations below the DNA (SEQ ID NO: 12).

```
<----------------------------------------LEADER-------------------------------------------\-
ATG GAC ACG AGG GTC CCC GCT CAG CTC CTG GGG CTG CTA ATG CTC TGG GTC CCA GGA TCC AGT
 M   D   T   R   V   P   A   Q   L   L   G   L   L   M   L   W   V   P   G   S   S

\--->  <---------------------------V_κII-----------------------------------------------\-
GGG GAT GTT GTG GTG ACT CAG TCT CCA CTC TCC CTG CCC GTC ACC CTT GGA CAG CCG GCC TCC
 G   D   V   V   V   T   Q   S   P   L   S   L   P   V   T   L   G   Q   P   A   S

\------------------*********************CDR1*********************************----\-
ATC TCC TGC AGA TCT AGT CTA AGC CTC GTG GAC AGT GAC GGA AAC ACC TAC TTG AAT TGG TTT
 I   S   C   R   S   S   L   S   L   V   D   S   D   G   N   T   Y   L   N   W   F

\-------------------------------------------------**********CDR2***********----\-
CTC CAG AGG CCA GGC CAA TCT CCA AGG CGC CTA ATT TAT CAG CTT TCT AGC CGG GAC TCT GGG
 L   Q   R   P   G   Q   S   P   R   R   L   I   Y   Q   L   S   S   R   D   S   G

\-----------------------------------------------------------------------------\-
GTC CCA GAC AGA TCC AGC GGC AGT GGG TCA GGC ACT GAT TTC ACT CTG AAA ATC AGC AGG GTG
 V   P   D   R   F   S   G   S   G   S   G   T   D   F   T   L   K   I   S   R   V

\-----------------------------------***********CDR3*********> <******--------\-
GAG GCT GAG GAT GTT GGC GTT TAT TAC TGC ATG CAA GGT ACA CAC TGG CCG ATC ACC TTC GGC
 E   A   E   D   V   G   V   Y   Y   C   M   Q   G   T   H   W   P   I   T   F   G

\----------J_κ5--------------------->
CAA GGG ACA CGA CTG GAG ATT AAA CGA
 Q   P   T   R   L   E   I   K   R
```

TABLE 9-3

DNA sequence of the V$_L$ region of ZM1-2 is shown below (SEQ ID NO: 13). The leader, VI and J regions are denoted by the dashed line; complementarity-determining regions CDR1, CDR2 and CDR3 are indicated by the asterisks. Amino acids appear as single letter abbreviations below the DNA (SEQ ID NO: 14).

```
<----------------------------LEADER-------------------------------------------> <--\-
ATG AGG CCC GTC GCT CAG CTC CTG GGG CTC CTG CTG CTC TGG TTC CCA GGT TCC AGA TGC GAC
 M   R   P   V   A   Q   L   L   G   L   L   L   L   W   F   P   G   S   R   C   D

\-----------------------------V_κI-----------------------------------------------\-
ATC CAG ATG ACC CAG TCT CCA TCT TCC GTG TCT GCA TCT GTG GGA GAC AGA GTC ACC GTC ACT
 I   Q   M   T   Q   S   P   S   S   V   S   A   S   V   G   D   R   V   T   V   T

\----***************CDR1*********************-------------------------------\-
TGT CGG GCG AGT CAG GGT ATT AGC AGT TGG TTA GCC TGG TAT CAG CAG AAA CCA GGG AAA GCC
 C   R   A   S   Q   G   I   S   S   W   L   A   W   Y   Q   Q   K   P   G   K   A

\----------------********CDR2**************-------------------------------\-
CCT AAA CTC CTG ATC CAT GCT GCA TCC AGT TTG CAA AGT GGG GTC CCA TCA AGG TTC ATC GGC
 P   K   L   L   I   H   A   A   S   S   L   Q   S   G   V   P   S   R   F   I   G

\-----------------------------------------------------------------------------\-
AGT GGA TCT GGG ACA GAT TTC ACT CTC ACC ATC ACC AGC CTG CAG GCT GAA GAT TTT GCA ACC
 S   G   S   G   T   D   F   T   L   T   I   T   S   L   Q   A   E   D   F   A   T

\--------*****************CDR3****> <*****---------------J_κ------------\-
TAC TAT TGT CAA CAG GCT GAC AGT CTC CCT TTT ACT TTC GGC GGA GGG ACC AAG GTG GAC TTC
 Y   Y   C   Q   Q   A   D   S   L   P   F   T   F   G   G   G   T   K   V   D   F
```

TABLE 9-3-continued

DNA sequence of the V_L region of ZM1-2 is shown below (SEQ ID NO: 13). The leader, VI and J regions are denoted by the dashed line; complementarity-determining regions CDR1, CDR2 and CDR3 are indicated by the asterisks. Amino acids appear as single letter abbreviations below the DNA (SEQ ID NO: 14).

\-----------\>

| AAA | CGA |
|-----|-----|
| K   | R   |

TABLE 9-4

DNA sequence of the V_L region of MD3-4 is shown below (SEQ ID NO: 15). The VIII and J3 regions are denoted by the dashed line; complementarity-determining regions CDR1, CDR2 and CDR3 are indicated by the asterisks. Amino acids appear as single letter abbreviations below the DNA (SEQ ID NO: 16).

<------------------------------------ V_λIII ------------------------------------\-

| CAG | TCT | CAG | CTG | ACG | CAG | CCT | GCC | TCA | GTG | TCC | GTG | TCC | CCA | GGA | CAG | ACA | GCC | AGC | ATC | ACC |
|-----|-----|-----|-----|-----|-----|-----|-----|-----|-----|-----|-----|-----|-----|-----|-----|-----|-----|-----|-----|-----|
| Q   | S   | Q   | L   | T   | Q   | P   | A   | S   | V   | S   | V   | S   | P   | G   | Q   | T   | A   | S   | I   | T   |

\-----------***********CDR1****************-----------------------------------\-

| TGC | TCT | GGA | GAT | AGA | TTG | GGG | GAT | GAA | TTT | GCT | TCC | TGG | TAT | CAG | CAG | AAG | CCA | GGC | CAG | TCC |
|-----|-----|-----|-----|-----|-----|-----|-----|-----|-----|-----|-----|-----|-----|-----|-----|-----|-----|-----|-----|-----|
| C   | S   | G   | D   | R   | L   | G   | D   | E   | F   | A   | S   | W   | Y   | Q   | Q   | K   | P   | G   | Q   | S   |

\----------------------------------********CDR2*********-----------------------\-

| CCT | ATT | CTG | GTC | ATC | TTT | GAG | GAT | AAC | AAG | AGG | CCC | TCA | GGG | ATC | CCT | GAA | CGA | TTC | TCT | GGC |
|-----|-----|-----|-----|-----|-----|-----|-----|-----|-----|-----|-----|-----|-----|-----|-----|-----|-----|-----|-----|-----|
| P   | I   | L   | V   | I   | F   | E   | D   | N   | K   | R   | P   | S   | G   | I   | P   | E   | R   | F   | S   | G   |

\-------------------------------------------------------------------------------\-

| TCC | AAC | TCT | GGG | AAC | ACA | GCC | ACT | CTG | ACC | ATC | AGC | GGG | ACC | CAG | GCT | ATG | GAT | GAG | GCT | GAC |
|-----|-----|-----|-----|-----|-----|-----|-----|-----|-----|-----|-----|-----|-----|-----|-----|-----|-----|-----|-----|-----|
| S   | N   | S   | G   | N   | T   | A   | T   | L   | T   | I   | S   | G   | T   | Q   | A   | M   | D   | E   | A   | D   |

\----------------*************CDR3\>\<***-------------- J_λ3 -------------\-

| TAT | TAC | TGT | CTG | GCG | TGG | GCC | AGC | AGC | CTT | TGG | GTG | TTC | GGC | GGA | GGG | ACC | AAG | CTG | ACC | GTC |
|-----|-----|-----|-----|-----|-----|-----|-----|-----|-----|-----|-----|-----|-----|-----|-----|-----|-----|-----|-----|-----|
| Y   | Y   | C   | L   | A   | W   | A   | S   | S   | L   | W   | V   | F   | G   | G   | G   | T   | K   | L   | T   | V   |

\---\>

| TTG |
|-----|
| L   |

---

What is claimed is:

1. A cell line designated ATCC HB 9234.

2. A human monoclonal antibody produced by the cell line designated ATCC HB 9234.

3. A Fab fragment of the human monoclonal antibody of claim 2.

4. A human monoclonal antibody comprising a heavy chain variable region having the amino acid sequence shown in Table 8-1 (SEQ ID NO:2) and a light chain variable region having the amino acid sequence shown in Table 9-1 (SEQ ID NO:10).

5. A cell line producing the antibody of claim 4.

6. A Fab fragment of the antibody of claim 4.

7. A composition comprising the antibody of claim 2 and a vehicle.

8. A composition comprising the antibody of claim 4 and a vehicle.

9. The human monoclonal antibody of claim 4, wherein the heavy chain variable region is encoded by the DNA sequence shown in Table 8-1 (SEQ ID NO:1) and the light chain variable domain is encoded by the DNA sequence shown in Table 9-1 (SEQ ID NO:9).

\* \* \* \* \*

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 423 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( G ) CELL TYPE: Hybridoma
        ( H ) CELL LINE: PE1-1

( i x ) FEATURE:

( A ) NAME/KEY: CDS
( B ) LOCATION: 1..423

( x i ) SEQUENCE DESCRIPTION: SEQ ID NO:1:

| ATG | GAG | TTT | GGG | CTG | AGC | TGG | GTT | TTC | CTC | GTT | GCT | CTT | TTA | AGA | GGT | 48 |
| Met | Glu | Phe | Gly | Leu | Ser | Trp | Val | Phe | Leu | Val | Ala | Leu | Leu | Arg | Gly | |
| 1 | | | | 5 | | | | | 10 | | | | | 15 | | |

| GTC | CAG | TGT | CAG | GTG | CAG | CTG | GTG | GAG | TCT | GGG | GGA | GGC | GTG | GTC | CAG | 96 |
| Val | Gln | Cys | Gln | Val | Gln | Leu | Val | Glu | Ser | Gly | Gly | Gly | Val | Val | Gln | |
| | | 20 | | | | | 25 | | | | | 30 | | | | |

| CCT | GGG | AGG | TCC | CTG | AGA | CTC | TCC | TGT | GCA | GCC | TCT | GGA | TTC | ACC | TTC | 144 |
| Pro | Gly | Arg | Ser | Leu | Arg | Leu | Ser | Cys | Ala | Ala | Ser | Gly | Phe | Thr | Phe | |
| | | 35 | | | | 40 | | | | | 45 | | | | | |

| AGT | AGG | TAT | GGC | ATG | CAC | TGG | GTC | CGC | CAG | GCT | CCA | GGC | AAG | GGG | CTG | 192 |
| Ser | Arg | Tyr | Gly | Met | His | Trp | Val | Arg | Gln | Ala | Pro | Gly | Lys | Gly | Leu | |
| | 50 | | | | | 55 | | | | | 60 | | | | | |

| GAG | TGG | GTG | GCA | GTG | ATA | TCA | TAT | GAT | GGA | AGT | AAT | AAA | TGG | TAT | GCA | 240 |
| Glu | Trp | Val | Ala | Val | Ile | Ser | Tyr | Asp | Gly | Ser | Asn | Lys | Trp | Tyr | Ala | |
| 65 | | | | | 70 | | | | | 75 | | | | | 80 | |

| GAC | TCC | GTG | AAG | GGC | CGA | TTC | ACC | ATC | TCC | AGA | GAC | AAT | TCC | AAG | AAC | 288 |
| Asp | Ser | Val | Lys | Gly | Arg | Phe | Thr | Ile | Ser | Arg | Asp | Asn | Ser | Lys | Asn | |
| | | | | 85 | | | | | 90 | | | | | 95 | | |

| ACT | CTG | TTT | CTG | CAA | ATG | CAC | AGC | CTG | AGA | GCT | GCG | GAC | ACG | GGT | GTA | 336 |
| Thr | Leu | Phe | Leu | Gln | Met | His | Ser | Leu | Arg | Ala | Ala | Asp | Thr | Gly | Val | |
| | | | 100 | | | | | 105 | | | | | 110 | | | |

| TAT | TAC | TGT | GCG | AAA | GAT | CAA | CTT | TAC | TTT | GGT | TCG | CAG | AGT | CCC | GGG | 384 |
| Tyr | Tyr | Cys | Ala | Lys | Asp | Gln | Leu | Tyr | Phe | Gly | Ser | Gln | Ser | Pro | Gly | |
| | | 115 | | | | | 120 | | | | | 125 | | | | |

| CAC | TAC | TGG | GTC | CAG | GGA | ACC | CTG | GTC | ACC | GTC | TCC | TCA | | | | 423 |
| His | Tyr | Trp | Val | Gln | Gly | Thr | Leu | Val | Thr | Val | Ser | Ser | | | | |
| | 130 | | | | | 135 | | | | | 140 | | | | | |

( 2 ) INFORMATION FOR SEQ ID NO:2:

( i ) SEQUENCE CHARACTERISTICS:
( A ) LENGTH: 141 amino acids
( B ) TYPE: amino acid
( D ) TOPOLOGY: linear ( i i ) MOLECULE TYPE: protein ( x i ) SEQUENCE DESCRIPTION: SEQ ID NO:2:

| Met | Glu | Phe | Gly | Leu | Ser | Trp | Val | Phe | Leu | Val | Ala | Leu | Leu | Arg | Gly |
| 1 | | | | 5 | | | | | 10 | | | | | 15 | |

| Val | Gln | Cys | Gln | Val | Gln | Leu | Val | Glu | Ser | Gly | Gly | Gly | Val | Val | Gln |
| | | 20 | | | | | 25 | | | | | 30 | | | |

| Pro | Gly | Arg | Ser | Leu | Arg | Leu | Ser | Cys | Ala | Ala | Ser | Gly | Phe | Thr | Phe |
| | | 35 | | | | 40 | | | | | 45 | | | | |

| Ser | Arg | Tyr | Gly | Met | His | Trp | Val | Arg | Gln | Ala | Pro | Gly | Lys | Gly | Leu |
| | 50 | | | | | 55 | | | | | 60 | | | | |

| Glu | Trp | Val | Ala | Val | Ile | Ser | Tyr | Asp | Gly | Ser | Asn | Lys | Trp | Tyr | Ala |
| 65 | | | | | 70 | | | | | 75 | | | | | 80 |

| Asp | Ser | Val | Lys | Gly | Arg | Phe | Thr | Ile | Ser | Arg | Asp | Asn | Ser | Lys | Asn |
| | | | | 85 | | | | | 90 | | | | | 95 | |

| Thr | Leu | Phe | Leu | Gln | Met | His | Ser | Leu | Arg | Ala | Ala | Asp | Thr | Gly | Val |
| | | | 100 | | | | | 105 | | | | | 110 | | |

| Tyr | Tyr | Cys | Ala | Lys | Asp | Gln | Leu | Tyr | Phe | Gly | Ser | Gln | Ser | Pro | Gly |
| | | 115 | | | | | 120 | | | | | 125 | | | |

| His | Tyr | Trp | Val | Gln | Gly | Thr | Leu | Val | Thr | Val | Ser | Ser |
| | 130 | | | | | 135 | | | | | 140 | |

( 2 ) INFORMATION FOR SEQ ID NO:3:

( i ) SEQUENCE CHARACTERISTICS:
        ( A ) LENGTH: 393 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( G ) CELL TYPE: Hybridoma
        ( H ) CELL LINE: ZM1-1

( i x ) FEATURE:
        ( A ) NAME/KEY: CDS
        ( B ) LOCATION: 1..393

( x i ) SEQUENCE DESCRIPTION: SEQ ID NO:3:

```
ATG GAG TTT GGG CTG AGC TGG GTT TTC CTT GTT GCT ATA TTA GAA GGT        48
Met Glu Phe Gly Leu Ser Trp Val Phe Leu Val Ala Ile Leu Glu Gly
        145                     150                     155

GTC CAG TGT GAG GTG CAG CTG GTG GAG TCT GGG GGA GGT TTG GTA CAG        96
Val Gln Cys Glu Val Gln Leu Val Glu Ser Gly Gly Gly Leu Val Gln
        160                     165                     170

CCT GGG GGG TCC CTG AGA CTC TCC TGT GCA GCC TCT GGA TTC ACC TTC       144
Pro Gly Gly Ser Leu Arg Leu Ser Cys Ala Ala Ser Gly Phe Thr Phe
        175                     180                     185

AGT AGG TAC GAC ATG TAC TGG GTC CGC CAA GCT ACA GGA AAA GGT CTG       192
Ser Arg Tyr Asp Met Tyr Trp Val Arg Gln Ala Thr Gly Lys Gly Leu
190                     195                     200                 205

GAG TGG GTC TCA GCT ATT GGT CCT ACT GGT GAC ACA TAC TAT GCA GAC       240
Glu Trp Val Ser Ala Ile Gly Pro Thr Gly Asp Thr Tyr Tyr Ala Asp
                    210                     215                 220

TCC GTG AAG GGC CGA TTC ACC ATC TCC AGA GAA AAT GCC AAG AAC TCC       288
Ser Val Lys Gly Arg Phe Thr Ile Ser Arg Glu Asn Ala Lys Asn Ser
                225                     230                 235

TTG TAT CTT ACA ATG AAC GGC CTG AGA GCC GGG GAC ACG GCT GTG TAT       336
Leu Tyr Leu Thr Met Asn Gly Leu Arg Ala Gly Asp Thr Ala Val Tyr
            240                     245                 250

TAC TGT GCA AGA GAT TTA GAA CTC TGG GGC CAG GGA ACC CTG GTC ACC       384
Tyr Cys Ala Arg Asp Leu Glu Leu Trp Gly Gln Gly Thr Leu Val Thr
    255                     260                 265

GTC TCC TCA                                                           393
Val Ser Ser
270
```

( 2 ) INFORMATION FOR SEQ ID NO:4:

( i ) SEQUENCE CHARACTERISTICS:
        ( A ) LENGTH: 131 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Glu Phe Gly Leu Ser Trp Val Phe Leu Val Ala Ile Leu Glu Gly
  1               5                    10                  15

Val Gln Cys Glu Val Gln Leu Val Glu Ser Gly Gly Gly Leu Val Gln
            20                  25                  30
```

| | | | | | | | | | | | | | | |
|---|---|---|---|---|---|---|---|---|---|---|---|---|---|---|
| Pro | Gly | Gly<br>35 | Ser | Leu | Arg | Leu | Ser<br>40 | Cys | Ala | Ala | Ser | Gly<br>45 | Phe | Thr | Phe |
| Ser | Arg<br>50 | Tyr | Asp | Met | Tyr | Trp<br>55 | Val | Arg | Gln | Ala | Thr<br>60 | Gly | Lys | Gly | Leu |
| Glu<br>65 | Trp | Val | Ser | Ala | Ile<br>70 | Gly | Pro | Thr | Gly | Asp<br>75 | Thr | Tyr | Tyr | Ala | Asp<br>80 |
| Ser | Val | Lys | Gly | Arg<br>85 | Phe | Thr | Ile | Ser | Arg<br>90 | Glu | Asn | Ala | Lys | Asn<br>95 | Ser |
| Leu | Tyr | Leu | Thr<br>100 | Met | Asn | Gly | Leu | Arg<br>105 | Ala | Gly | Asp | Thr | Ala<br>110 | Val | Tyr |
| Tyr | Cys | Ala<br>115 | Arg | Asp | Leu | Glu | Leu<br>120 | Trp | Gly | Gln | Gly | Thr<br>125 | Leu | Val | Thr |
| Val | Ser | Ser<br>130 | | | | | | | | | | | | | |

(2) INFORMATION FOR SEQ ID NO:5:

(i) SEQUENCE CHARACTERISTICS:
  (A) LENGTH: 402 base pairs
  (B) TYPE: nucleic acid
  (C) STRANDEDNESS: unknown
  (D) TOPOLOGY: unknown (ii) MOLECULE TYPE: cDNA (iii) HYPOTHETICAL: NO (iv) ANTI-SENSE: NO (vi) ORIGINAL SOURCE:
  (A) ORGANISM: Homo sapiens
  (G) CELL TYPE: Hybridoma
  (H) CELL LINE: ZM1-2

(ix) FEATURE:
  (A) NAME/KEY: CDS
  (B) LOCATION: 1..402

(xi) SEQUENCE DESCRIPTION: SEQ ID NO:5:

| | | | | | | | | | | | | | | | | |
|---|---|---|---|---|---|---|---|---|---|---|---|---|---|---|---|---|
| ATG | AAA | CAC | CTG | TGG | TTC | TTC | CTC | CTG | CTG | GTG | GCA | GTT | CCC | AGA | TGG | 48 |
| Met | Lys | His | Leu<br>135 | Trp | Phe | Phe | Leu | Leu<br>140 | Leu | Val | Ala | Val | Pro<br>145 | Arg | Trp | |
| GTC | GTG | TCC | CAG | GTG | CAG | CTG | CAG | GAG | TCG | GGC | CCA | GGA | CTG | GTG | AAG | 96 |
| Val | Val | Ser<br>150 | Gln | Val | Gln | Leu | Gln<br>155 | Glu | Ser | Gly | Pro | Gly<br>160 | Leu | Val | Lys | |
| GCT | GCG | GAG | ACC | CTG | TCC | CTC | ACC | TGC | ACT | GTC | TCC | CGT | GGC | TCC | TTC | 144 |
| Ala | Ala | Glu<br>165 | Thr | Leu | Ser | Leu | Thr<br>170 | Cys | Thr | Val | Ser | Arg<br>175 | Gly | Ser | Phe | |
| AGT | GAT | TAC | TTC | TGG | AAT | TGG | TTC | CGG | CAG | CCC | GCC | GGG | AAG | CGC | CTG | 192 |
| Ser | Asp<br>180 | Tyr | Phe | Trp | Asn<br>185 | Trp | Phe | Arg | Gln | Pro<br>190 | Ala | Gly | Lys | Arg | Leu<br>195 | |
| GAG | TGG | CTT | GGG | CGT | GTC | TAT | ACC | AGT | GGA | AGT | GTC | GAC | TAC | AAC | CCC | 240 |
| Glu | Trp | Leu | Gly | Arg<br>200 | Val | Tyr | Thr | Ser | Gly<br>205 | Ser | Val | Asp | Tyr | Asn<br>210 | Pro | |
| TCC | CTC | AAG | AGT | CGA | GTC | ACC | GTG | TCA | GTG | GAC | ACG | TCC | AAG | AAG | CAG | 288 |
| Ser | Leu | Lys | Ser<br>215 | Arg | Val | Thr | Val | Ser<br>220 | Val | Asp | Thr | Ser | Lys<br>225 | Lys | Gln | |
| TTC | TCC | CTG | AGG | CTG | AGC | TCT | GTG | ACC | GTC | GCG | GAC | ACG | GCC | GTG | TAT | 336 |
| Phe | Ser | Leu | Arg<br>230 | Leu | Ser | Ser | Val | Thr<br>235 | Val | Ala | Asp | Thr | Ala<br>240 | Val | Tyr | |
| TAT | TGT | GCG | AGA | GGA | CTG | TCC | GGT | TTT | GAC | TAC | TGG | GGC | CAG | GGA | GCC | 384 |
| Tyr | Cys | Ala<br>245 | Arg | Gly | Leu | Ser | Gly<br>250 | Phe | Asp | Tyr | Trp | Gly<br>255 | Gln | Gly | Ala | |
| CTG | GTC | ACC | GTC | TCC | CCA | | | | | | | | | | | 402 |

```
Leu  Val  Thr  Val  Ser  Pro
260                 265
```

( 2 ) INFORMATION FOR SEQ ID NO:6:

( i ) SEQUENCE CHARACTERISTICS:
        ( A ) LENGTH: 134 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Lys  His  Leu  Trp  Phe  Phe  Leu  Leu  Leu  Val  Ala  Val  Pro  Arg  Trp
 1              5                        10                            15

Val  Val  Ser  Gln  Val  Gln  Leu  Gln  Glu  Ser  Gly  Pro  Gly  Leu  Val  Lys
               20                       25                       30

Ala  Ala  Glu  Thr  Leu  Ser  Leu  Thr  Cys  Thr  Val  Ser  Arg  Gly  Ser  Phe
          35                       40                       45

Ser  Asp  Tyr  Phe  Trp  Asn  Trp  Phe  Arg  Gln  Pro  Ala  Gly  Lys  Arg  Leu
     50                       55                       60

Glu  Trp  Leu  Gly  Arg  Val  Tyr  Thr  Ser  Gly  Ser  Val  Asp  Tyr  Asn  Pro
65                       70                       75                       80

Ser  Leu  Lys  Ser  Arg  Val  Thr  Val  Ser  Val  Asp  Thr  Ser  Lys  Lys  Gln
               85                       90                       95

Phe  Ser  Leu  Arg  Leu  Ser  Ser  Val  Thr  Val  Ala  Asp  Thr  Ala  Val  Tyr
               100                      105                      110

Tyr  Cys  Ala  Arg  Gly  Leu  Ser  Gly  Phe  Asp  Tyr  Trp  Gly  Gln  Gly  Ala
          115                      120                      125

Leu  Val  Thr  Val  Ser  Pro
     130
```

( 2 ) INFORMATION FOR SEQ ID NO:7:

( i ) SEQUENCE CHARACTERISTICS:
        ( A ) LENGTH: 441 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( G ) CELL TYPE: Hybridoma
        ( H ) CELL LINE: MD3-4

( i x ) FEATURE:
        ( A ) NAME/KEY: CDS
        ( B ) LOCATION: 1..441

( x i ) SEQUENCE DESCRIPTION: SEQ ID NO:7:

```
ATG  GGG  TCA  ACC  GCC  ATC  CTT  GGC  CTC  CTC  CTG  GCT  GTT  CTC  CAA  GGA       48
Met  Gly  Ser  Thr  Ala  Ile  Leu  Gly  Leu  Leu  Leu  Ala  Val  Leu  Gln  Gly
135                      140                      145                      150

GTC  TGT  GCC  GAA  GTG  CAG  CTG  GTG  CAA  TCT  GGA  GCA  GAG  GTG  AAA  AAG       96
Val  Cys  Ala  Glu  Val  Gln  Leu  Val  Gln  Ser  Gly  Ala  Glu  Val  Lys  Lys
               155                      160                      165

CCC  GGG  GAG  TCT  CTG  AGG  ATC  TCC  TGT  AAG  GGT  TCT  GGA  TAC  AGC  TTT      144
Pro  Gly  Glu  Ser  Leu  Arg  Ile  Ser  Cys  Lys  Gly  Ser  Gly  Tyr  Ser  Phe
               170                      175                      180
```

| | | | | | | | | | | | | | | | |
|---|---|---|---|---|---|---|---|---|---|---|---|---|---|---|---|
| ACC | AGC | TAC | TGG | ATC | AGC | TGG | GTG | CGC | CAG | ATG | CCC | GGG | AAG | GGC | CTG | 192
| Thr | Ser | Tyr | Trp | Ile | Ser | Trp | Val | Arg | Gln | Met | Pro | Gly | Lys | Gly | Leu |
| | | 185 | | | | 190 | | | | | 195 | | | | |
| GAG | TGG | ATG | GGG | AGG | CTT | GAT | CCT | AGT | GCC | TCC | TCT | GCC | ATC | TTC | AGC | 240
| Glu | Trp | Met | Gly | Arg | Leu | Asp | Pro | Ser | Ala | Ser | Ser | Ala | Ile | Phe | Ser |
| | | 200 | | | | 205 | | | | | 210 | | | | |
| CCG | TCC | CTC | CAA | GGC | CAC | GTC | ACC | ATC | TCA | GTT | GAC | AAG | TCC | ATG | AGG | 288
| Pro | Ser | Leu | Gln | Gly | His | Val | Thr | Ile | Ser | Val | Asp | Lys | Ser | Met | Arg |
| 215 | | | | | 220 | | | | | 225 | | | | | 230 |
| ACT | GCC | TAC | GTG | CAG | TGG | AGA | AGC | CTG | AAG | GCC | TCG | GAC | ACC | GCC | ATG | 336
| Thr | Ala | Tyr | Val | Gln | Trp | Arg | Ser | Leu | Lys | Ala | Ser | Asp | Thr | Ala | Met |
| | | | | 235 | | | | | 240 | | | | | 245 | |
| TAT | TAC | TGT | GCG | AGA | CAT | GTC | CGC | GAA | AAG | AGT | ATG | GTT | CAG | GGA | GTC | 384
| Tyr | Tyr | Cys | Ala | Arg | His | Val | Arg | Glu | Lys | Ser | Met | Val | Gln | Gly | Val |
| | | | 250 | | | | | 255 | | | | | 260 | | |
| ATT | ATA | AAG | GAC | GCT | TTT | GAT | ATC | TGG | GGC | CAA | GGG | ACA | ATG | GTC | ACC | 432
| Ile | Ile | Lys | Asp | Ala | Phe | Asp | Ile | Trp | Gly | Gln | Gly | Thr | Met | Val | Thr |
| | | 265 | | | | 270 | | | | | 275 | | | | |
| GTC | TCT | TCA | | | | | | | | | | | | | | 441
| Val | Ser | Ser | | | | | | | | | | | | | |
| | | 280 | | | | | | | | | | | | | |

( 2 ) INFORMATION FOR SEQ ID NO:8:

( i ) SEQUENCE CHARACTERISTICS:
        ( A ) LENGTH: 147 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Gly | Ser | Thr | Ala | Ile | Leu | Gly | Leu | Leu | Leu | Ala | Val | Leu | Gln | Gly |
| 1 | | | | 5 | | | | | 10 | | | | | 15 | |
| Val | Cys | Ala | Glu | Val | Gln | Leu | Val | Gln | Ser | Gly | Ala | Glu | Val | Lys | Lys |
| | | | 20 | | | | | 25 | | | | | 30 | | |
| Pro | Gly | Glu | Ser | Leu | Arg | Ile | Ser | Cys | Lys | Gly | Ser | Gly | Tyr | Ser | Phe |
| | | 35 | | | | | 40 | | | | | 45 | | | |
| Thr | Ser | Tyr | Trp | Ile | Ser | Trp | Val | Arg | Gln | Met | Pro | Gly | Lys | Gly | Leu |
| | 50 | | | | | 55 | | | | | 60 | | | | |
| Glu | Trp | Met | Gly | Arg | Leu | Asp | Pro | Ser | Ala | Ser | Ser | Ala | Ile | Phe | Ser |
| 65 | | | | | 70 | | | | | 75 | | | | | 80 |
| Pro | Ser | Leu | Gln | Gly | His | Val | Thr | Ile | Ser | Val | Asp | Lys | Ser | Met | Arg |
| | | | | 85 | | | | | 90 | | | | | 95 | |
| Thr | Ala | Tyr | Val | Gln | Trp | Arg | Ser | Leu | Lys | Ala | Ser | Asp | Thr | Ala | Met |
| | | | 100 | | | | | 105 | | | | | 110 | | |
| Tyr | Tyr | Cys | Ala | Arg | His | Val | Arg | Glu | Lys | Ser | Met | Val | Gln | Gly | Val |
| | | 115 | | | | | 120 | | | | | 125 | | | |
| Ile | Ile | Lys | Asp | Ala | Phe | Asp | Ile | Trp | Gly | Gln | Gly | Thr | Met | Val | Thr |
| | | 130 | | | | 135 | | | | | 140 | | | | |
| Val | Ser | Ser | | | | | | | | | | | | | |
| 145 | | | | | | | | | | | | | | | |

( 2 ) INFORMATION FOR SEQ ID NO:9:

( i ) SEQUENCE CHARACTERISTICS:
        ( A ) LENGTH: 324 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens
    ( G ) CELL TYPE: Hybridoma ( i x ) FEATURE:
    ( A ) NAME/KEY: CDS
    ( B ) LOCATION: 1..324

( x i ) SEQUENCE DESCRIPTION: SEQ ID NO:9:

```
CAG TCT CAG CTG ACG CAG CCG CCC TCG GTG TCA GTG GCC CCA GGG CAG    48
Gln Ser Gln Leu Thr Gln Pro Pro Ser Val Ser Val Ala Pro Gly Gln
    150                 155                 160

ACG GCC AGG ATT ACC TGT GGG GGA GAC AAC ATT GGG AGT AAA AGT GTG    96
Thr Ala Arg Ile Thr Cys Gly Gly Asp Asn Ile Gly Ser Lys Ser Val
    165                 170                 175

AAC TGG TTC CAG CAG AAG CCA GGC CAG GCC CCT GTC CTG GTC GTC TAT   144
Asn Trp Phe Gln Gln Lys Pro Gly Gln Ala Pro Val Leu Val Val Tyr
180                 185                 190                 195

GAT GAT AAC GAA CGG CCC TCA GGC ATT TCT GAG CGA TTC TCT GGC TCC   192
Asp Asp Asn Glu Arg Pro Ser Gly Ile Ser Glu Arg Phe Ser Gly Ser
                200                 205                 210

AAC TCT GGG AAC ACG GCC ACC CTG ACC ATC AGC AGG GTC GAA GCC GGG   240
Asn Ser Gly Asn Thr Ala Thr Leu Thr Ile Ser Arg Val Glu Ala Gly
            215                 220                 225

GAT GAG GCC GAC TAT TAC TGT CAG GTG TGG GAT AGT AGT AGT GAT CAT   288
Asp Glu Ala Asp Tyr Tyr Cys Gln Val Trp Asp Ser Ser Ser Asp His
        230                 235                 240

GTG GTA TTC GGC GGA GGG ACC AAG CTG ACC GTC CTA                   324
Val Val Phe Gly Gly Gly Thr Lys Leu Thr Val Leu
    245                 250                 255
```

( 2 ) INFORMATION FOR SEQ ID NO:10:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Gln Ser Gln Leu Thr Gln Pro Pro Ser Val Ser Val Ala Pro Gly Gln
  1                 5                  10                  15

Thr Ala Arg Ile Thr Cys Gly Gly Asp Asn Ile Gly Ser Lys Ser Val
                 20                  25                  30

Asn Trp Phe Gln Gln Lys Pro Gly Gln Ala Pro Val Leu Val Val Tyr
             35                  40                  45

Asp Asp Asn Glu Arg Pro Ser Gly Ile Ser Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu
                100                 105
```

( 2 ) INFORMATION FOR SEQ ID NO:11:

( i ) SEQUENCE CHARACTERISTICS:

(A) LENGTH: 405 base pairs
(B) TYPE: nucleic acid
(C) STRANDEDNESS: unknown
(D) TOPOLOGY: unknown (ii) MOLECULE TYPE: cDNA (iii) HYPOTHETICAL: NO (iv) ANTI-SENSE: NO (vi) ORIGINAL SOURCE:
(A) ORGANISM: Homo sapiens
(G) CELL TYPE: Hybridoma
(H) CELL LINE: ZM1-1

(ix) FEATURE:
(A) NAME/KEY: CDS
(B) LOCATION: 1..405

(xi) SEQUENCE DESCRIPTION: SEQ ID NO:11:

| | | | | | | | | | | | | | | | | |
|---|---|---|---|---|---|---|---|---|---|---|---|---|---|---|---|---|
| ATG | GAC | ACG | AGG | GTC | CCC | GCT | CAG | CTC | CTG | GGG | CTG | CTA | ATG | CTC | TGG | 48 |
| Met | Asp | Thr | Arg | Val | Pro | Ala | Gln | Leu | Leu | Gly | Leu | Leu | Met | Leu | Trp | |
| 110 | | | | 115 | | | | | | 120 | | | | | | |
| GTC | CCA | GGA | TCC | AGT | GGG | GAT | GTT | GTG | GTG | ACT | CAG | TCT | CCA | CTC | TCC | 96 |
| Val | Pro | Gly | Ser | Ser | Gly | Asp | Val | Val | Val | Thr | Gln | Ser | Pro | Leu | Ser | |
| 125 | | | | | 130 | | | | | 135 | | | | | 140 | |
| CTG | CCC | GTC | ACC | CTT | GGA | CAG | CCG | GCC | TCC | ATC | TCC | TGC | AGA | TCT | AGT | 144 |
| Leu | Pro | Val | Thr | Leu | Gly | Gln | Pro | Ala | Ser | Ile | Ser | Cys | Arg | Ser | Ser | |
| | | | | 145 | | | | | 150 | | | | | 155 | | |
| CTA | AGC | CTC | GTG | GAC | AGT | GAC | GGA | AAC | ACC | TAC | TTG | AAT | TGG | TTT | CTC | 192 |
| Leu | Ser | Leu | Val | Asp | Ser | Asp | Gly | Asn | Thr | Tyr | Leu | Asn | Trp | Phe | Leu | |
| | | | 160 | | | | | 165 | | | | | 170 | | | |
| CAG | AGG | CCA | GGC | CAA | TCT | CCA | AGG | CGC | CTA | ATT | TAT | CAG | CTT | TCT | AGC | 240 |
| Gln | Arg | Pro | Gly | Gln | Ser | Pro | Arg | Arg | Leu | Ile | Tyr | Gln | Leu | Ser | Ser | |
| | | 175 | | | | | 180 | | | | | 185 | | | | |
| CGG | GAC | TCT | GGG | GTC | CCA | GAC | AGA | TTC | AGC | GGC | AGT | GGG | TCA | GGC | ACT | 288 |
| Arg | Asp | Ser | Gly | Val | Pro | Asp | Arg | Phe | Ser | Gly | Ser | Gly | Ser | Gly | Thr | |
| | 190 | | | | | 195 | | | | | 200 | | | | | |
| GAT | TTC | ACT | CTG | AAA | ATC | AGC | AGG | GTG | GAG | GCT | GAG | GAT | GTT | GGC | GTT | 336 |
| Asp | Phe | Thr | Leu | Lys | Ile | Ser | Arg | Val | Glu | Ala | Glu | Asp | Val | Gly | Val | |
| 205 | | | | | 210 | | | | | 215 | | | | | 220 | |
| TAT | TAC | TGC | ATG | CAA | GGT | ACA | CAC | TGG | CCG | ATC | ACC | TTC | GGC | CAA | GGG | 384 |
| Tyr | Tyr | Cys | Met | Gln | Gly | Thr | His | Trp | Pro | Ile | Thr | Phe | Gly | Gln | Gly | |
| | | | | 225 | | | | | 230 | | | | | 235 | | |
| ACA | CGA | CTG | GAG | ATT | AAA | CGA | | | | | | | | | | 405 |
| Thr | Arg | Leu | Glu | Ile | Lys | Arg | | | | | | | | | | |
| | | | 240 | | | | | | | | | | | | | |

(2) INFORMATION FOR SEQ ID NO:12:

(i) SEQUENCE CHARACTERISTICS:
(A) LENGTH: 135 amino acids
(B) TYPE: amino acid
(D) TOPOLOGY: linear (ii) MOLECULE TYPE: protein (xi) SEQUENCE DESCRIPTION: SEQ ID NO:12:

| | | | | | | | | | | | | | | |
|---|---|---|---|---|---|---|---|---|---|---|---|---|---|---|
| Met | Asp | Thr | Arg | Val | Pro | Ala | Gln | Leu | Leu | Gly | Leu | Leu | Met | Leu | Trp |
| 1 | | | | 5 | | | | | 10 | | | | | 15 | |
| Val | Pro | Gly | Ser | Ser | Gly | Asp | Val | Val | Val | Thr | Gln | Ser | Pro | Leu | Ser |
| | | | 20 | | | | | 25 | | | | | 30 | | |
| Leu | Pro | Val | Thr | Leu | Gly | Gln | Pro | Ala | Ser | Ile | Ser | Cys | Arg | Ser | Ser |
| | | | 35 | | | | | 40 | | | | | 45 | | |
| Leu | Ser | Leu | Val | Asp | Ser | Asp | Gly | Asn | Thr | Tyr | Leu | Asn | Trp | Phe | Leu |

|   |   |   |   |   | 50 |   |   |   |   | 55 |   |   |   |   | 60 |   |   |   |   |
|---|---|---|---|---|----|---|---|---|---|----|---|---|---|---|----|---|---|---|---|

Gln Arg Pro Gly Gln Ser Pro Arg Arg Leu Ile Tyr Gln Leu Ser Ser
65                  70                  75                  80

Arg Asp Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Gly Thr His Trp Pro Ile Thr Phe Gly Gln Gly
        115                 120                 125

Thr Arg Leu Glu Ile Lys Arg
    130             135

( 2 ) INFORMATION FOR SEQ ID NO:13:

( i ) SEQUENCE CHARACTERISTICS:
        ( A ) LENGTH: 384 base pairs
        ( B ) TYPE: nucleic acid
        ( C ) STRANDEDNESS: unknown
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( G ) CELL TYPE: Hybridoma
        ( H ) CELL LINE: ZM1-2

( i x ) FEATURE:
        ( A ) NAME/KEY: CDS
        ( B ) LOCATION: 1..384

( x i ) SEQUENCE DESCRIPTION: SEQ ID NO:13:

ATG AGG CCC GTC GCT CAG CTC CTG GGG CTC CTG CTG CTC TGG TTC CCA        48
Met Arg Pro Val Ala Gln Leu Leu Gly Leu Leu Leu Leu Trp Phe Pro
            140                 145                 150

GGT TCC AGA TGC GAC ATC CAG ATG ACC CAG TCT CCA TCT TCC GTG TCT        96
Gly Ser Arg Cys Asp Ile Gln Met Thr Gln Ser Pro Ser Ser Val Ser
            155                 160                 165

GCA TCT GTG GGA GAC AGA GTC ACC GTC ACT TGT CGG GCG AGT CAG GGT       144
Ala Ser Val Gly Asp Arg Val Thr Val Thr Cys Arg Ala Ser Gln Gly
            170                 175                 180

ATT AGC AGT TGG TTA GCC TGG TAT CAG CAG AAA CCA GGG AAA GCC CCT       192
Ile Ser Ser Trp Leu Ala Trp Tyr Gln Gln Lys Pro Gly Lys Ala Pro
            185                 190                 195

AAA CTC CTG ATC CAT GCT GCA TCC AGT TTG CAA AGT GGG GTC CCA TCA       240
Lys Leu Leu Ile His Ala Ala Ser Ser Leu Gln Ser Gly Val Pro Ser
200                 205                 210                 215

AGG TTC ATC GGC AGT GGA TCT GGG ACA GAT TTC ACT CTC ACC ATC ACC       288
Arg Phe Ile Gly Ser Gly Ser Gly Thr Asp Phe Thr Leu Thr Ile Thr
            220                 225                 230

AGC CTG CAG GCT GAA GAT TTT GCA ACC TAC TAT TGT CAA CAG GCT GAC       336
Ser Leu Gln Ala Glu Asp Phe Ala Thr Tyr Tyr Cys Gln Gln Ala Asp
            235                 240                 245

AGT CTC CCT TTT ACT TTC GGC GGA GGG ACC AAG GTG GAC TTC AAA CGA       384
Ser Leu Pro Phe Thr Phe Gly Gly Gly Thr Lys Val Asp Phe Lys Arg
            250                 255                 260

( 2 ) INFORMATION FOR SEQ ID NO:14:

( i ) SEQUENCE CHARACTERISTICS:
        ( A ) LENGTH: 128 amino acids 5,565,354

43                                                                                                     44
-continued ( B ) TYPE: amino acid
( D ) TOPOLOGY: linear ( i i ) MOLECULE TYPE: protein ( x i ) SEQUENCE DESCRIPTION: SEQ ID NO:14:

| Met | Arg | Pro | Val | Ala | Gln | Leu | Leu | Gly | Leu | Leu | Leu | Trp | Phe | Pro |
|---|---|---|---|---|---|---|---|---|---|---|---|---|---|---|
| 1 | | | | 5 | | | | | 10 | | | | | 15 |

| Gly | Ser | Arg | Cys | Asp | Ile | Gln | Met | Thr | Gln | Ser | Pro | Ser | Ser | Val | Ser |
|---|---|---|---|---|---|---|---|---|---|---|---|---|---|---|---|
| | | | 20 | | | | | 25 | | | | | 30 | | |

| Ala | Ser | Val | Gly | Asp | Arg | Val | Thr | Val | Thr | Cys | Arg | Ala | Ser | Gln | Gly |
|---|---|---|---|---|---|---|---|---|---|---|---|---|---|---|---|
| | | 35 | | | | | 40 | | | | | 45 | | | |

| Ile | Ser | Ser | Trp | Leu | Ala | Trp | Tyr | Gln | Gln | Lys | Pro | Gly | Lys | Ala | Pro |
|---|---|---|---|---|---|---|---|---|---|---|---|---|---|---|---|
| | 50 | | | | | 55 | | | | | 60 | | | | |

| Lys | Leu | Leu | Ile | His | Ala | Ala | Ser | Ser | Leu | Gln | Ser | Gly | Val | Pro | Ser |
|---|---|---|---|---|---|---|---|---|---|---|---|---|---|---|---|
| 65 | | | | | 70 | | | | | 75 | | | | | 80 |

| Arg | Phe | Ile | Gly | Ser | Gly | Ser | Gly | Thr | Asp | Phe | Thr | Leu | Thr | Ile | Thr |
|---|---|---|---|---|---|---|---|---|---|---|---|---|---|---|---|
| | | | | 85 | | | | | 90 | | | | | 95 | |

| Ser | Leu | Gln | Ala | Glu | Asp | Phe | Ala | Thr | Tyr | Tyr | Cys | Gln | Gln | Ala | Asp |
|---|---|---|---|---|---|---|---|---|---|---|---|---|---|---|---|
| | | | 100 | | | | | 105 | | | | | 110 | | |

| Ser | Leu | Pro | Phe | Thr | Phe | Gly | Gly | Gly | Thr | Lys | Val | Asp | Phe | Lys | Arg |
|---|---|---|---|---|---|---|---|---|---|---|---|---|---|---|---|
| | | 115 | | | | | 120 | | | | | 125 | | | |

( 2 ) INFORMATION FOR SEQ ID NO:15:

( i ) SEQUENCE CHARACTERISTICS:
( A ) LENGTH: 318 base pairs
( B ) TYPE: nucleic acid
( C ) STRANDEDNESS: unknown
( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Homo sapiens
( G ) CELL TYPE: Hybridoma
( H ) CELL LINE: MD3-4

( i x ) FEATURE:
( A ) NAME/KEY: CDS
( B ) LOCATION: 1..318

( x i ) SEQUENCE DESCRIPTION: SEQ ID NO:15:

| CAG | TCT | CAG | CTG | ACG | CAG | CCT | GCC | TCA | GTG | TCC | GTG | TCC | CCA | GGA | CAG | 48 |
|---|---|---|---|---|---|---|---|---|---|---|---|---|---|---|---|---|
| Gln | Ser | Gln | Leu | Thr | Gln | Pro | Ala | Ser | Val | Ser | Val | Ser | Pro | Gly | Gln | |
| 130 | | | | | 135 | | | | | 140 | | | | | | |

| ACA | GCC | AGC | ATC | ACC | TGC | TCT | GGA | GAT | AGA | TTG | GGG | GAT | GAA | TTT | GCT | 96 |
|---|---|---|---|---|---|---|---|---|---|---|---|---|---|---|---|---|
| Thr | Ala | Ser | Ile | Thr | Cys | Ser | Gly | Asp | Arg | Leu | Gly | Asp | Glu | Phe | Ala | |
| 145 | | | | 150 | | | | | 155 | | | | | 160 | | |

| TCC | TGG | TAT | CAG | CAG | AAG | CCA | GGC | CAG | TCC | CCT | ATT | CTG | GTC | ATC | TTT | 144 |
|---|---|---|---|---|---|---|---|---|---|---|---|---|---|---|---|---|
| Ser | Trp | Tyr | Gln | Gln | Lys | Pro | Gly | Gln | Ser | Pro | Ile | Leu | Val | Ile | Phe | |
| | | | 165 | | | | | 170 | | | | | 175 | | | |

| GAG | GAT | AAC | AAG | AGG | CCC | TCA | GGG | ATC | CCT | GAA | CGA | TTC | TCT | GGC | TCC | 192 |
|---|---|---|---|---|---|---|---|---|---|---|---|---|---|---|---|---|
| Glu | Asp | Asn | Lys | Arg | Pro | Ser | Gly | Ile | Pro | Glu | Arg | Phe | Ser | Gly | Ser | |
| | | | 180 | | | | | 185 | | | | | 190 | | | |

| AAC | TCT | GGG | AAC | ACA | GCC | ACT | CTG | ACC | ATC | AGC | GGG | ACC | CAG | GCT | ATG | 240 |
|---|---|---|---|---|---|---|---|---|---|---|---|---|---|---|---|---|
| Asn | Ser | Gly | Asn | Thr | Ala | Thr | Leu | Thr | Ile | Ser | Gly | Thr | Gln | Ala | Met | |
| | | 195 | | | | | 200 | | | | | 205 | | | | |

| GAT | GAG | GCT | GAC | TAT | TAC | TGT | CTG | GCG | TGG | GCC | AGC | AGC | CTT | TGG | GTG | 288 |
|---|---|---|---|---|---|---|---|---|---|---|---|---|---|---|---|---|
| Asp | Glu | Ala | Asp | Tyr | Tyr | Cys | Leu | Ala | Trp | Ala | Ser | Ser | Leu | Trp | Val | |
| | 210 | | | | | 215 | | | | | 220 | | | | | |

```
TTC  GGC  GGA  GGG  ACC  AAG  CTG  ACC  GTC  TTG                                    318
Phe  Gly  Gly  Gly  Thr  Lys  Leu  Thr  Val  Leu
225                      230
```

( 2 ) INFORMATION FOR SEQ ID NO:16:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Gln  Ser  Gln  Leu  Thr  Gln  Pro  Ala  Ser  Val  Ser  Val  Ser  Pro  Gly  Gln
 1                    5                   10                       15

Thr  Ala  Ser  Ile  Thr  Cys  Ser  Gly  Asp  Arg  Leu  Gly  Asp  Glu  Phe  Ala
               20                   25                        30

Ser  Trp  Tyr  Gln  Gln  Lys  Pro  Gly  Gln  Ser  Pro  Ile  Leu  Val  Ile  Phe
          35                        40                   45

Glu  Asp  Asn  Lys  Arg  Pro  Ser  Gly  Ile  Pro  Glu  Arg  Phe  Ser  Gly  Ser
     50                        55                   60

Asn  Ser  Gly  Asn  Thr  Ala  Thr  Leu  Thr  Ile  Ser  Gly  Thr  Gln  Ala  Met
65                        70                   75                            80

Asp  Glu  Ala  Asp  Tyr  Tyr  Cys  Leu  Ala  Trp  Ala  Ser  Ser  Leu  Trp  Val
                    85                        90                        95

Phe  Gly  Gly  Gly  Thr  Lys  Leu  Thr  Val  Leu
               100                      105
```